(12) United States Patent
Bae et al.

(10) Patent No.: US 10,513,545 B2
(45) Date of Patent: Dec. 24, 2019

(54) FUSION POLYPEPTIDE IN WHICH ANTI-INFLAMMATORY POLYPEPTIDE AND FERRITIN MONOMER FRAGMENT ARE BOUND AND PHARMACEUTICAL COMPOSITION FOR PREVENTING AND TREATING INFLAMMATORY DISEASES, CONTAINING SAME AS ACTIVE INGREDIENT

(71) Applicants: KYUNGPOOK NATIONAL UNIVERSITY INDUSTRY-ACADEMIC COOPERATION FOUNDATION, Daegu (KR); KOREA INSTITUTE OF SCIENCE AND TECHNOLOGY, Seoul (KR)

(72) Inventors: Jong-Sup Bae, Daegu (KR); In-San Kim, Daegu (KR); Won Hwa Lee, Changwon-si (KR); Jun Young Seo, Daegu (KR); So Youn Kim, Daegu (KR)

(73) Assignees: KYUNGPOOK NATIONAL UNIVERSITY INDUSTRY-ACADEMIC COOPERATION FOUNDATION, Daegu (KR); KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 15/757,580

(22) PCT Filed: Sep. 2, 2016

(86) PCT No.: PCT/KR2016/009845
§ 371 (c)(1),
(2) Date: Jun. 8, 2018

(87) PCT Pub. No.: WO2017/039383
PCT Pub. Date: Mar. 9, 2017

(65) Prior Publication Data
US 2019/0016764 A1 Jan. 17, 2019

(30) Foreign Application Priority Data
Sep. 2, 2015 (KR) .......................... 10-2015-0124472

(51) Int. Cl.
| | | |
|---|---|---|
| C07K 14/47 | (2006.01) |
| A61K 38/16 | (2006.01) |
| A61K 38/17 | (2006.01) |
| C07K 14/54 | (2006.01) |
| C07K 14/79 | (2006.01) |
| C07K 19/00 | (2006.01) |
| A61K 47/64 | (2017.01) |
| A61P 29/00 | (2006.01) |
| C12N 15/62 | (2006.01) |
| A61K 38/20 | (2006.01) |
| A61K 38/40 | (2006.01) |

(52) U.S. Cl.
CPC .............. *C07K 14/47* (2013.01); *A61K 38/16* (2013.01); *A61K 38/17* (2013.01); *A61K 47/644* (2017.08); *A61P 29/00* (2018.01); *C07K 14/54* (2013.01); *C07K 14/5406* (2013.01); *C07K 14/5431* (2013.01); *C07K 14/5437* (2013.01); *C07K 14/79* (2013.01); *C07K 19/00* (2013.01); *C12N 15/62* (2013.01); *A61K 38/2006* (2013.01); *A61K 38/2026* (2013.01); *A61K 38/2073* (2013.01); *A61K 38/2086* (2013.01); *A61K 38/40* (2013.01); *Y02A 50/40* (2018.01)

(58) Field of Classification Search
CPC ................................ C07K 14/47; A61K 38/16
See application file for complete search history.

(56) References Cited

U.S. PATENT DOCUMENTS

2011/0287033 A1* 11/2011 Connor .................. A61K 33/26
424/178.1

FOREIGN PATENT DOCUMENTS

| KR | 10-1189192 B1 | 10/2012 |
|---|---|---|
| KR | 10-2013-0062168 A | 6/2013 |

(Continued)

OTHER PUBLICATIONS

International Search Report of PCT/KR2016/009845 dated Dec. 1, 2016 [PCT/ISA/210].

(Continued)

*Primary Examiner* — Amber D Steele
(74) *Attorney, Agent, or Firm* — Sughrue Mion, PLLC

(57) ABSTRACT

The present invention relates to: a fusion polypeptide in which an anti-inflammatory polypeptide and a ferritin monomer fragment are bound; and a pharmaceutical composition for treating inflammatory diseases, containing the same as an active ingredient and, more specifically, to: a fusion polypeptide in which an anti-inflammatory polypeptide is fused to an N-terminus and/or a C-terminus of a ferritin monomer fragment from which a portion of a fourth loop and a fifth helix, of a human derived ferritin monomer, are removed; and a use thereof for treating inflammatory diseases. As in the above, the fusion polypeptide, which has an amino acid sequence represented by SEQ ID NO: 1 and in which an anti-inflammatory polypeptide is fused to an N-terminus and/or a C-terminus of a fragment of a human-derived ferritin monomer, can fuse two types of anti-inflammatory polypeptides, acting through different mechanisms, into a nano cage and administer the same, and thus the fusion polypeptide can exhibit an excellent effect in the treatment of inflammatory diseases including sepsis.

8 Claims, 19 Drawing Sheets
(5 of 19 Drawing Sheet(s) Filed in Color)
Specification includes a Sequence Listing.

(56) References Cited

FOREIGN PATENT DOCUMENTS

| KR | 10-2014-0101319 A | 8/2014 |
| KR | 10-1477123 B1 | 12/2014 |
| KR | 10-2015-0088597 A | 8/2015 |

OTHER PUBLICATIONS

Written Opinion of PCT/KR2016/009845 dated Dec. 1, 2016 [PCT/ISA/237].
Gutte et al., The Total Synthesis of an Enzyme with Ribonuclease A Activity, Journal of the American Chemical Society, 91:2, Jan. 15, 1969, pp. 501-502.
Kent, Stephen B. H., Chemical Synthesis of Peptides and Proteins, Ann. Rev. Biochem. 57, 1988, pp. 957-989.

\* cited by examiner

FUSION POLYPEPTIDE IN WHICH ANTI-INFLAMMATORY POLYPEPTIDE AND FERRITIN MONOMER FRAGMENT ARE BOUND AND PHARMACEUTICAL COMPOSITION FOR PREVENTING AND TREATING INFLAMMATORY DISEASES, CONTAINING SAME AS ACTIVE INGREDIENT

CROSS REFERENCE TO RELATED APPLICATIONS

The present application is a National Stage of International Application No. PCT/KR2016/009845, filed on Sep. 2, 2016, which claims priority from Korean Patent Application No. 10-2015-0124472, filed on Sep. 2, 2015, the entire contents of which are incorporated herein by reference.

TECHNICAL FIELD

The present invention relates to: a fusion polypeptide in which an anti-inflammatory polypeptide and a ferritin monomer fragment are bound, and a use thereof. More specifically, the present invention relates to a fusion polypeptide in which an anti-inflammatory polypeptide is fused to a N-terminus and/or C-terminus of a human-derived ferritin monomer fragment in which a portion of a fourth loop and a fifth helix a human-derived ferritin monomer are removed, and a use thereof for treating inflammatory diseases.

BACKGROUND OF THE INVENTION

Inflammation reaction is collectively referred to as a defensive reaction of a living body to restore the structure and function of its tissues damaged by infection, trauma and the like. Mobilization of leukocyte cells to the site of inflammation is important for the rapid resolution of the infection and the repair of tissue damages resulting from various traumas. However, erroneous or persistent inflammatory reactions may cause damage and disease to the tissues of the body. For example, inflammatory diseases may result from infections caused by bacteria or viruses such as cerebrospinal meningitis, enteritis, dermatitis, uveitis, encephalitis, adult respiratory distress syndrome, or non-infective factors such as trauma, autoimmune diseases and organ transplant rejection. Inflammatory diseases are classified into acute and chronic inflammatory diseases which have different symptoms and pathological features, respectively. Local symptoms of acute inflammation such as allergies, bacterial and viral infections include changes in blood flow and blood vessel size, changes in vascular permeability and leukocyte infiltration. On the other hand, the main pathological features of chronic inflammation such as rheumatoid arthritis, atherosclerosis, chronic nephritis and liver cirrhosis are that inflammatory factors are not removed and thus monocytes, neutrophils, lymphocytes and plasma cells continuously infiltrate into inflammation sites, resulting in rendering the inflammation reaction chronic.

Inflammatory mediators expressed in inflammatory sites such as cytokines, chemokines, reactive oxygen intermediates, cyclooxygenase-2 (COX-2), 5-lipoxygenase (5-LOX), and matrix metalloproteinase (MMP) play an important role in the generation and maintenance of inflammatory reactions. Expression of these inflammatory mediators is mediated by transcription factors such as NF-κB (nuclear factor KB), STAT3 (signal transducer and activator of transcription 3), AP-1 (activator protein 1), and HIF-1a (hypoxia-inducible factor 1a).

Sepsis, on the other hand, is a systemic inflammatory reaction caused by an abnormal defense of the body against an infected microorganism. The activation of macrophages is associated with excessive production of inflammatory factors, leading to a severe inflammatory response in the whole body. When there are shown at least two symptoms of a fever with body temperature rising 38° C. or above, hypothermia with body temperature falling to 36° C. or below, a respiratory rate of at least 24 breaths per minute (tachypnea), a pulse rate of at least 90 beats per minute (tachycardia), and a blood test result showing an increase or a marked decrease in leukocyte count, it is called a systemic inflammatory response syndrome (SIRS). it is called sepsis when the systemic inflammatory response syndrome is caused by microbial infection. The sepsis can potentially lead to a septic shock. When sepsis gets worse, the function of various organs (heart, kidney, liver, brain, lungs, etc.) of the body deteriorates. If it gets much worse, it may lead to a shock state. The sepsis may be caused by various types of pathogens. Its highest incidence is induced by bacteria, while being also caused by viruses or fungi. There are pneumonia causing an infection in the lungs, urinary tract infection causing an infection in the bladder and kidneys, cellulitis occurring in skin, appendicitis occurring in the abdomen, or meningitis occurring in the brain, and the like. For example, if a patient with pneumonia has sepsis, his/her brain, heart, liver, lungs, or kidneys can be damaged, while about 20-50% of patients die from septic shock if severe progression occurs. In addition, the sepsis may occur by a post-operative infection. 40 to 90% of patients may die in case a sepsis occurs as a hyperacute inflammatory response due to infection or a postoperative infection.

It is understood that the sepsis occurs as a result of complex interactions between causative organisms and host immune, inflammation and coagulation systems. Both the response of the host and the characteristics of the causative organisms have a significant impact on the prognosis of sepsis. Organ failure observed in sepsis occurs when the host inadequately reacts to causative organisms. If the host's response to the causative organisms is over-amplified, it can lead to organ damage in the host itself. Based on this concept, antagonistic substances against proinflammatory cytokines such as TNF-α, IL-1β and IL-6, which play a leading role in host inflammation, have been applied as a treatment for sepsis, but most of them found unsuccessful. Further, mechanical ventilation, the administration of activated protein C (C), and glucocorticoid treatment have been also tried, but various limitations have been revealed.

Therefore, there is a need for a new therapeutic agent for preventing or treating sepsis and septic shock with a high mortality rate, for which a definite therapeutic agent has yet to be developed.

DETAILED DESCRIPTION OF THE INVENTION

Technical Problem

Accordingly, the present inventors have completed the present invention after they constructed a fusion polypeptide in which an anti-inflammatory polypeptide is fused to a N-terminus and/or a C-terminus of a human-derived ferritin monomer fragment (short ferritin, sFt) in which a portion of a fourth loop and a fifth helix of a human-derived ferritin monomer are removed, finding that the fusion polypeptide is capable of fusing different polypeptide medicinal agents at its N-terminus or C-terminus, and forming a nano-cage via self-assembling even after the fusion to effectively deliver the medicinal agents.

An aspect of the present invention is to provide a fusion polypeptide in which an anti-inflammatory polypeptide is fused to C-terminus, N-terminus, or C-terminus and N-terminus of a human-derived ferritin monomer fragment having an amino acid sequence represented by SEQ ID NO: 1, wherein the anti-inflammatory polypeptide is at least one selected from the group consisting of a thrombin receptor agonist peptide (TRAP), a Protein C Gla domain (PC-Gla) polypeptide, a human beta-defensin-3 (hBD3), an interleukin-1 receptor antagonist (IL-1ra), interleukin-4 (IL-4), interleukin-11 (IL-11), interleukin-13 (IL-13), TSG-6 (TNF-a-stimulated gene 6 protein), a C1 inhibitor, an Activated Protein C (APC), a parotid secretory protein (PSP) and a fragment thereof.

Another aspect of the present invention is to provide a polynucleotide encoding the fusion polypeptide.

Still another aspect of the present invention is to provide an expression vector comprising the polynucleotide.

Still another aspect of the present invention is to provide a transformant transformed with the expression vector.

Further another aspect of the present invention is to provide a protein cage comprising the fusion polypeptide, wherein an anti-inflammatory polypeptide protrudes outside the protein cage.

Still another aspect of the present invention is to provide a pharmaceutical composition for treating an inflammatory disease, the composition comprising the fusion polypeptide as an active ingredient.

Still another aspect of the present invention is to provide use of the fusion polypeptide for preparing an agent for treating an inflammatory disease.

Still further another aspect of the present invention is to provide a method for treating an inflammatory disease in a subject in need thereof, the method comprising administering an effective amount of a composition comprising the fusion polypeptide as an active ingredient to a subject in need thereof.

Technical Solution

An embodiment according to an aspect of the present invention is to provide a fusion polypeptide in which an anti-inflammatory polypeptide is fused to C-terminus, N-terminus, or C-terminus and N-terminus of a human-derived ferritin monomer fragment having an amino acid sequence represented by SEQ ID NO: 1, wherein the anti-inflammatory polypeptide is at least one selected from the group consisting of a thrombin receptor agonist peptide (TRAP), a Protein C Gla domain (PC-Gla) polypeptide, a human beta-defensin-3 (hBD3), an interleukin-1 receptor antagonist (IL-1ra), interleukin-4 (IL-4), interleukin-11 (IL-11), interleukin-13 (IL-13), TSG-6 (TNF-a-stimulated gene 6 protein), a C1 inhibitor, an Activated Protein C (APC), a parotid secretory protein (PSP) and a fragment thereof.

Another embodiment according to an aspect of the present invention provides a polynucleotide encoding the fusion polypeptide.

Still another embodiment according to an aspect of the present invention provides an expression vector comprising the polynucleotide.

Still another embodiment according to an aspect of the present invention provides a transformant transformed with the expression vector.

An embodiment according to another aspect of the present invention provides a protein cage comprising the fusion polypeptide, wherein an anti-inflammatory polypeptide protrudes outside the protein cage.

Another embodiment according to an aspect of the present invention provides a pharmaceutical composition for treating an inflammatory disease, the composition comprising the fusion polypeptide as an active ingredient.

Still another embodiment according to an aspect of the present invention provides a pharmaceutical composition for treating an inflammatory disease, the composition consisting of the fusion polypeptide.

Still another embodiment according to an aspect of the present invention provides a pharmaceutical composition for treating an inflammatory disease, the composition consisting essentially of the fusion polypeptide.

An embodiment according to still another aspect of the present invention provides a use of the fusion polypeptide for preparing an agent for treating an inflammatory disease.

Another embodiment according to an aspect of the present invention provides a method for treating an inflammatory disease in a subject in need thereof, the method comprising administering an effective amount of a composition comprising the fusion polypeptide as an active ingredient to a subject in need thereof.

Another embodiment according to an aspect of the present invention provides a method for treating an inflammatory disease in a subject in need thereof, the method comprising administering an effective amount of a composition consisting of the fusion polypeptide as an active ingredient to a subject in need thereof.

Still another embodiment according to an aspect of the present invention provides a method for treating an inflammatory disease in a subject in need thereof, the method comprising administering an effective amount of a composition consisting essentially of the fusion polypeptide as an active ingredient to a subject in need thereof.

Hereinafter, the present invention will be described in detail.

An embodiment according to The present invention is to provide a fusion polypeptide in which an anti-inflammatory polypeptide is fused to C-terminus, N-terminus, or C-terminus and N-terminus of a human-derived ferritin monomer fragment having an amino acid sequence represented by SEQ ID NO: 1, wherein the anti-inflammatory polypeptide is at least one selected from the group consisting of a thrombin receptor agonist peptide (TRAP), a Protein C Gla domain (PC-Gla) polypeptide, a human beta-defensin-3 (hBD3), an interleukin-1 receptor antagonist (IL-1ra), interleukin-4 (IL-4), interleukin-11 (IL-11), interleukin-13 (IL-13), TSG-6 (TNF-a-stimulated gene 6 protein), a C1 inhibitor, an Activated Protein C (APC), a parotid secretory protein (PSP) and a fragment thereof.

SEQ ID NO: 1 (human-derived ferritin heavy chain monomer fragment):

```
MTTASTSQVR QNYHQDSEAA INRQINLELY ASYVYLSMSY
YFDRDDVALK NFAKYFLHQS HEEREHAEKL MKLQNQRGGR
IFLQDIKKPD CDDWESGLNA MECALHLEKN VNQSLLELHK
LATDKNDPHL CDFIETHYLN EQVKAIKELG DHVTNLRKMG A
```

Ferritin is an intracellular protein which stores and releases iron. Ferritin exists generally in the form of a hollow spherical cage in vivo, wherein the cage is composed of 24 ferritin monomers which are classified into heavy chain and light chain depending on their structure.

In an embodiment according to the present invention, the human-derived ferritin monomer fragment having the amino acid sequence of SEQ ID NO: 1 is composed of the 1st to 161th amino acids of the human-derived ferritin heavy chain monomer having the amino acid sequence of SEQ ID NO: 2, which is a short ferritin (sFt) in which a portion of a fourth loop and a fifth helix of ferritin heavy chain monomer are removed.

The amino acid sequence of SEQ ID NO: 2 is as follows:
SEQ ID NO: 2 (heavy chain monomer of human-derived ferritin, GenBank: AAA35832.1):

```
MTTASTSQVR QNYHQDSEAA INRQINLELY ASYVYLSMSY

YFDRDDVALK NFAKYFLHQS HEEREHAEKL MKLQNQRGGR

IFLQDIKKPD CDDWESGLNA MECALHLEKN VNQSLLELHK

LATDKNDPHL CDFIETHYLN EQVKAIKELG DHVTNLRKMG

APESGLAEYL FDKHTLGDSD NES
```

Although the monomer fragment of the human-derived ferritin having the amino acid sequence shown in SEQ ID NO: 1 is a modified form in which some polypeptides are removed from the wild-type ferritin monomer, a steric hindrance is considerably alleviated to reduce a restriction on the size of a peptide or protein which may be fused to its C-terminus, while maintaining the inherent characteristics of ferritin which forms a protein cage by self-assembling. In the present invention, the anti-inflammatory fusion polypeptide having a remarkably improved therapeutic effect was prepared by fusing a polypeptide showing anti-inflammatory activity not only at the N-terminus but also at the C-terminus of the ferritin monomer fragment.

In the fusion polypeptide according to the present invention, an anti-inflammatory polypeptide of the same or different type may be fused to each of the N-terminus or C-terminus of the human-derived ferritin monomer fragment. The anti-inflammatory polypeptide may be appropriately selected for the preparation of the fusion polypeptide by those skilled in the art, depending on the type of inflammatory disease to be treated and the pharmacological mechanism of the polypeptide to be fused.

In an embodiment according to the present invention, the fusion polypeptide may be prepared by a method known to those skilled in the art. Such fusion polypeptides may be produced in prokaryotic or eukaryotic cells by expressing polynucleotides encoding the fusion polypeptide sequences of the present invention, often as a part of larger polypeptides. Alternatively, such fusion polypeptides may be synthesized by chemical methods. Methods for expression of heterologous proteins in recombinant hosts, chemical synthesis of polypeptides and in vitro transcription are well known in the art and are further described in the literatures (Reference: Maniatis et al., Molecular Cloning: A Laboratory Manual (1989), 2nd Ed., Cold Sprin Harbor, N.Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91:501; Chaiken I. M. (1981) CRC Crit. Rev. Biochem. 11: 255; Kaiser et al. (1989) Ann. Rev. Biochem. 57:957; and Offord, R. E. (1980) Semisynthetic Proteins, Wiley Publishing).

In an embodiment according to the present invention, the type of the anti-inflammatory polypeptide capable of being fused to the N-terminus and/or the C-terminus of the human-derived ferritin monomer fragment is not particularly limited. It may include not only conventional polypeptides known to exhibit anti-inflammatory activity in the art, but also new anti-inflammatory polypeptides to be identified in the future. The anti-inflammatory polypeptide is not particularly limited in its size, while it may be a short peptide fragment or a protein.

Non-limiting examples of such anti-inflammatory polypeptides include a thrombin receptor agonist peptide (TRAP), a Protein C Gla domain (PC-Gla) polypeptide, a human beta-defensin-3 (hBD3), an interleukin-1 receptor antagonist (IL-1ra), interleukin-4 (IL-4), interleukin-11 (IL-11), interleukin-13 (IL-13), TSG-6 (TNF-a-stimulated gene 6 protein), a C1 inhibitor, an Activated Protein C (APC), a parotid secretory protein (PSP), together with a fragment thereof exhibiting the same physiological activity as the polypeptide.

In an embodiment according to the present invention, the TRAP may have an amino acid sequence of SEQ ID NO: 3:

```
(TFLLRN)
```

In an embodiment according to the present invention, the PC-Gla polypeptide may have an amino acid sequence of SEQ ID NO: 4:

```
(ANSFLEELRHSSLERECIEEICDFEEAKEIFQNVDDTLAFWSKHV)
```

In an embodiment according to the present invention, human beta-defensin-3 (hBD3) may have an amino acid sequence of SEQ ID NO: 5:

```
(MRIHYLLFAL LFLFLVPVPG HGGIINTLQK YYCRVRGGRC
AVLSCLPKEE QIGKCSTRGR KCCRRKK)
```

In an embodiment according to the present invention, the IL-1 receptor antagonist (IL-1ra) may have an amino acid sequence of SEQ ID NO: 6:

```
(MEICRGLRSH LITLLLFLFH SETICRPSGR KSSKMQAFRI

WDVNQKTFYL RNNQLVAGYL QGPNVNLEEK IDVVPIEPHA

LFLGIHGGKM CLSCVKSGDE TRLQLEAVNI TDLSENRKQD

KRFAFIRSDS GPTTSFESAA CPGWFLCTAM EADQPVSLTN

MPDEGVMVTK FYFQEDE)
```

In an embodiment according to the present invention, the interleukin-4 (IL-4) may have an amino acid sequence of SEQ ID NO: 7:

```
(MGLTSQLLPP LFFLLACAGN FVHGHKCDIT LQEIIKTLNS

LTEQKNTTEK ETFCRAATVL RQFYSHHEKD TRCLGATAQQ

FHRHKQLIRF LKRLDRNLWG LAGLNSCPVK EANQSTLENF

LERLKTIMRE KYSKCSS)
```

In an embodiment according to the present invention, the interleukin-11 (IL-11) may have an amino acid sequence of SEQ ID NO: 8:

(MNCVCRLVLV VLSLWPDTAV APGPPPGPPR VSPDPRAELD

STVLLTRSLL ADTRQLAAQL RDKFPADGDH NLDSLPTLAM

SAGALGALQL PGVLTRLRAD LLSYLRHVQW LRRAGGSSLK

TLEPELGTLQ ARLDRLLRRL QLLMSRLALP QPPPDPPAPP

LAPPSSAWGG IRAAHAILGG LHLTLDWAVR GLLLLKTRL)

In an embodiment according to the present invention, the interleukin-13 (IL-13) may have an amino acid sequence of SEQ ID NO: 9:

(MALLLTTVIA LTCLGGFASP GPVPPSTALR ELIEELVNIT

QNQKRPLCNG SMVWSINLTA GMYCAALESL INVSGCSAIE

KTQRMLSGFC PHKVSAGFSS LHVRDTKIEV AQFVKDLLLH

LKKLFREGRF N)

In an embodiment according to the present invention, the TSG-6 (TNF-a-stimulated gene 6 protein) may have an amino acid sequence of SEQ ID NO: 10:

(MIILIYLFLL LWEDTQGWGF KDGIFHNSIW LERAAGVYHR

EARSGKYKLT YAEAKAVCEF EGGHLATYKQ LEAARKIGFH

VCAAGWMAKG RVGYPIVKPG PNCGFGKTGI IDYGIRLNRS

ERWDAYCYNP HAKECGGVFT DPKQIFKSPG FPNEYEDNQI

CYWHIRLKYG QRIHLSFLDF DLEDDPGCLA DYVEIYDSYD

DVHGFVGRYC GDELPDDIIS TGNVMTLKFL SDASVTAGGF

QIKYVAMDPV SKSSQGKNTS TTSTGNKNFL AGRFSHL)

In an embodiment according to the present invention, the Activated Protein C (APC) may have an amino acid sequence of SEQ ID NO: 11:

(MWQLTSLLLF VATWGISGTP APLDSVFSSS ERAHQVLRIR

KRANSFLEEL RHSSLERECI EEICDFEEAK EIFQNVDDTL

AFWSKHVDGD QCLVLPLEHP CASLCCGHGT CIDGIGSFSC

DCRSGWEGRF CQREVSFLNC SLDNGGCTHY CLEEVGWRRC

SCAPGYKLGD DLLQCHPAVK FPCGRPWKRM EKKRSHLKRD

TEDQEDQVDP RLIDGKMTRR GDSPWQVVLL DSKKKLACGA

VLIHPSWVLT AAHCMDESKK LLVRLGEYDL RRWEKWELDL

DIKEVFVHPN YSKSTTDNDI ALLHLAQPAT LSQTIVPICL

PDSGLAEREL NQAGQETLVT GWGYHSSREK EAKRNRTFVL

NFIKIPVVPH NECSEVMSNM VSENMLCAGI LGDRQDACEG

DSGGPMVASF HGTWFLVGLV SWGEGCGLLH NYGVYTKVSR

YLDWIHGHIR DKEAPQKSWA P)

In an embodiment according to the present invention the parotid secreted protein (PSP) may be characterized by having an amino acid sequence of SEQ ID NO: 12:

(MLQLWKLVLL CGVLTGTSES LLDNLGNDLS NVVDKLEPVL

HEGLETVDNT LKGILEKLKV DLGVLQKSSA WQLAKQKAQE

AEKLLNNVIS KLLPTNTDIF GLKISNSLIL DVKAEPIDDG

KGLNLSFPVT ANVTVAGPII GQIINLKASL DLLTAVTIET

DPQTHQPVAV LRECASDPTS ISLSLLDKHS QIINKFVNSV

INTLKSTVSS LLQKEICPLI RIFIHSLDVN VIQQVVDNPQ

HKTQLQTLI)

In addition, functional equivalents of a thrombin receptor agonist peptide (TRAP), a Protein C Gla domain (PC-Gla) polypeptide, a human beta-defensin-3 (hBD3), an interleukin-1 receptor antagonist (IL-1ra), interleukin-4 (IL-4), interleukin-11 (IL-11), interleukin-13 (IL-13), TSG-6 (TNF-a-stimulated gene 6 protein), a C1 inhibitor, an Activated Protein C (APC), and a parotid secretory protein (PSP) are also included within the scope of the present invention. As used herein, the functional equivalents refer to a peptide exhibiting substantially the same activity as the above polypeptides, having at least 60%, preferably at least 70%, more preferably at least 80%, and most preferably at least 90% sequence homology with the amino acid sequence of SEQ ID NOS: 3-12, respectively, as a result of addition, substitution or deletion of amino acids.

The present invention provides the fusion polypeptide in which the anti-inflammatory polypeptide is fused to the human-derived ferritin monomer fragment having an amino acid sequence of SEQ ID NO: 1 through a linker.

The present invention also provides the fusion polypeptide wherein the linker is a substrate for MMP (matrix metalloproteinase).

As used herein, the MMP substrate is preferably selected from the group consisting of MMP1 substrate, MMP2 substrate, MMP3 substrate, MMP7 substrate, MMP8 substrate, MMP9 substrate, MMP12 substrate, MMP13 substrate and consensus substrate, while it may be more preferably MMP2 substrate.

The MMP substrate refers to a short amino acid chain which is degraded by matrix metalloproteinase (MMP). MMPs include about 19 kinds of various enzymes, and classified into four types of collagenase, gelatinase, stromelysin, and membrane type MMP (MT-MMP), respectively. Collagenase-1 (MMP-1), Collagenase-2 (MMP-8) and Collagenase-3 (MMP-13) are known as major collagenases which break down circular collagens.

Various types of MMPs are associated with inflammatory diseases depending on diseases. MMP-9 is associated with endotoxin shock in acute inflammatory diseases, while MMP-2 and MMP-9 are associated with multiple sclerosis in chronic inflammatory diseases. MMP-2, MMP-3, MMP-7, MMP-9, MMP-12, and MMP-13 are associated with atherosclerosis including stroke and myocardial infarction, while MMP-2 and MMP-9 are involved in restenosis of the mitral valve. MMP-8 and MMP-9 are involved in periodontitis and peri-implantitis. MMP-12 are involved in chronic obstructive pulmonary disease, while MMP-2, MMP-8, and MMP-9 are involved in asthma. MMP-7 and MMP-12 are associated with pulmonary fibrosis, while MMP-2, MMP-3, MMP-8, and MMP-9 are involved in hepatitis. MMP-2, MMP-8, MMP-9 and the like are associated with pancreatitis and meningitis (Jialiang Hu. et al., Nat. Rev. Drug. Discov. 6:480-498, 2007). Thus, effective MMP substrates may be different depending on the type of disease.

As used herein, the MMP substrate refers to a short peptide which is degraded by MMP. It specifically refers to MMP1 substrate, MMP2 substrate, MMP3 substrate, MMP7 substrate, MMP8 substrate, MMP9 substrate, MMP12 substrate, MMP13 substrate, MMP common substrate and the like. The MMP1 substrate refers to a short amino acid chain which is degraded by MMP-1. MMP2 substrate refers to a short amino acid chain which is degraded by MMP-2. MMP3 substrate refers to a short amino acid chain which is degraded by MMP-3. MMP7 substrate refers to a short amino acid chain which is degraded by MMP-7. MMP8 substrate refers to a short amino acid chain which is degraded by MMP-8. MMP9 substrate refers to a short amino acid chain which is degraded by MMP-9. MMP12 substrate refers to a short amino acid chain which is degraded by MMP-12. MMP13 substrate refers to a short amino acid chain which is degraded by MMP-13. The MMP consensus substrate refers to a short amino acid chain which is degraded by MMP-1, MMP-2, and MMP-3, respectively.

In the present invention, the linker which can be a substrate for MMP may have the amino acid sequence of SEQ ID NO: 13, wherein the amino acid sequence of SEQ ID NO: 13 is as follows:

SEQ ID NO: 13 (a linker containing a MMP2 cleavage site)

GPLGLAG

The present invention also provides a fusion polypeptide which has an amino acid sequence represented by SEQ ID NO: 14 or 15.

The amino acid sequences of SEQ ID NOS: 14 and 15 are as follows, respectively:

SEQ ID NOS: 14

MGGTTFLLRNASGHMSSQIRQNYSTDVEAAVNSLVNLYLQASYTYLSLGF

YFDRDDVALEGVSHFFRELAEEKREGYERLLKMQNQRGGRIFLQDIKKPA

EDEWGKTPDAMKAAMALEKKLNQALLDLHALGSARTDPHLCDFLETHFLD

EEVKLIKKMGDHLTNLHRLGGGSEFVDGGGSGTSANSFLEELRHSSLERE

CIEEICDFEEAKEIFQNVDDTLAFWSKHVLEHHHHHH

SEQ ID NOS: 15:

MGGTTFLLRNASGHMSSQIRQNYSTDVEAAVNSLVNLYLQASYTYLSLGF

YFDRDDVALEGVSHFFRELAEEKREGYERLLKMQNQRGGRIFLQDIKKPA

EDEWGKTPDAMKAAMALEKKLNQALLDLHALGSARTDPHLCDFLETHFLD

EEVKLIKKMGDHLTNLHRLGGGSEFVDGGGSGTSGPLGLAGANSFLEELR

HSSLERECIEEICDFEEAKEIFQNVDDTLAFWSKHVLEHHHHHH

An embodiment of the present invention provides a polynucleotide encoding the fusion polypeptide. The polynucleotide according to the present invention may be any base sequences which encode the fusion polypeptide according to the present invention.

An embodiment of the present invention also provides an expression vector comprising the polynucleotide according to the present invention.

As used herein, the expression vector is characterized by comprising the polynucleotide of the present invention, while its includes, but is not limited to, a plasmid vector, a cosmid vector, a bacteriophage vector, and a viral vector.

The expression vector of the present invention may be a conventional expression vector. The expression vector may contain an expression regulatory sequence such as a promoter, an operator, an initiation codon, a termination codon, a polyadenylation signal and an enhancer (promoter gene), as well as a signal sequence or leader sequence for membrane targeting or secretion, while it may be variously prepared according to its purpose. The promoter of the expression vector may be constitutive or inducible. The vector also comprises a selection marker for selecting a host cell containing the vector, while it contains the origin of replication if it is a replicable vector.

Another embodiment of the present invention also provides a transformant transformed with the expression vector according to the present invention.

The transformant of the present invention is characterized by being transformed with the expression vector of the present invention. Transformation with the above expression vector can be carried out by transformation techniques known to a person skilled in the art. Preferably, microprojectile bombardment, electroporation, calcium phosphate ($CaPO_4$) precipitation, calcium chloride ($CaCl_2$) precipitation, PEG-mediated fusion, microinjection, and a liposome-mediated method may be used. The transformant may be *Escherichia coli, Bacillus subtilis, Streptomyces, Pseudomonas, Proteus mirabilis, Staphylococcus*, and *Agrobacterium tumefaciens*, but are not limited thereto.

Meanwhile, another embodiment of the present invention provides a protein cage comprising the fusion polypeptide, wherein the anti-inflammatory polypeptide protrudes outside the protein cage.

Still another embodiment of the present invention provides a protein cage consisting of the fusion polypeptide, wherein the anti-inflammatory polypeptide protrudes outside the protein cage.

Still another embodiment of the present invention provides a protein cage consisting essentially of the fusion polypeptide, wherein the anti-inflammatory polypeptide protrudes outside the protein cage.

As used herein, the protein cage is a cage composed of protein which is formed by the precise self-assembling of low molecular weight monomers and possesses an internal space. It includes viral capsid protein, ferritin, heat shock protein, and Dps protein. The protein cage according to the present invention is characterized in that it comprises the fusion polypeptide of the present invention as a monomer constituting the protein cage. As used herein, the term 'self-assembling' refers to the property of a certain molecule with which the molecule forms a specific nanostructure by itself without any external stimulation or artificial induction.

The protein cage of the present invention is prepared by binding of the fusion polypeptide of the present invention and is generally in the form of a spherical cage in vivo.

The protein cage of the present invention may be a complex protein in which the fusion polypeptide of the present invention is regularly arranged as a unit. More preferably, the protein cage may be formed by regularly arranging 24 fusion polypeptides of the present invention three-dimensionally. Meanwhile, when the fusion polypeptide of the present invention forms a protein cage by self-assembling, the anti-inflammatory polypeptide fused to the N-terminus and/or the C-terminus of the ferritin monomer fragment may protrude through the outer surface of the cage protein and exhibit a physiological activity by easily binding to a target receptor or protein. Alternatively, the linker may be cleaved by MMP in a living tissue showing an inflammatory disease so that the anti-inflammatory polypeptide is dissociated from the protein cage to exhibit its own physiological activity.

An embodiment of the present invention also provides a pharmaceutical composition for treating an inflammatory disease, the composition comprising the fusion polypeptide as an active ingredient.

Another embodiment of the present invention provides a pharmaceutical composition for treating an inflammatory disease, the composition consisting of the fusion polypeptide as an active ingredient.

Still another embodiment of the present invention provides a pharmaceutical composition for treating an inflammatory disease, the composition consisting essentially of the fusion polypeptide as an active ingredient.

The pharmaceutical composition according to the present invention may be formulated into a suitable form by comprising the fusion peptide alone or in combination with a pharmaceutically acceptable carrier, and may further contain an excipient or a diluent. The term "pharmaceutically acceptable" as used herein refers to a non-toxic composition that is physiologically acceptable and does not cause allergic reactions such as gastrointestinal disorder or dizziness, or a similar reaction when administered to humans.

The pharmaceutically acceptable carrier may further include, for example, a carrier for oral administration or for parenteral administration. The carrier for oral administration may include lactose, starch, cellulose derivatives, magnesium stearate and stearic acid. In addition, it may include various drug delivery materials used for oral administration of peptide agents. In addition, the carrier for parenteral administration may include water, suitable oil, a saline solution, an aqueous glucose and a glycol, and may further contain a stabilizer and a preservative. Suitable stabilizers include antioxidants such as sodium hydrogen sulfite, sodium sulfite and ascorbic acid. Suitable preservatives include benzalkonium chloride, methyl- or propyl-paraben and chlorobutanol. The pharmaceutical composition of the present invention may further include a lubricant, a wetting agent, a sweetener, a flavoring agent, an emulsifying agent, and a suspending agent, in addition to the above components. Regarding other pharmaceutically acceptable carriers and preparations, the following literature may be referred (Remington's Pharmaceutical Sciences, 19th ed., Mack Publishing Company, Easton, Pa., 1995).

The composition of the present invention may be administered to mammals including humans by any method. For example, it may be administered orally or parenterally. Parenteral administration methods include, but are not limited to, intravenous, intramuscular, intra-arterial, intramedullary, intradural, intracardiac, transdermal, subcutaneous, intraperitoneal, intranasal, intestinal, topical, sublingual or rectal administration.

The pharmaceutical composition of the present invention may be formulated into oral or parenteral preparations according to the route of administration as described above.

In the case of oral preparations, the composition of the present invention may be formulated into powder, granules, tablets, pills, sugar-coated tablets, capsules, liquids, gels, syrups, slurries, suspensions or the like by using methods known in the art. For example, oral preparations may be obtained as tablets or sugar-coated tablets by combining the active ingredient with a solid excipient, pulverizing it, adding suitable auxiliaries, and then processing the mixture into a granular mixture. Examples of suitable excipients include sugars including lactose, dextrose, sucrose, sorbitol, mannitol, xylitol, erythritol and maltitol; starches including corn starch, wheat starch, rice starch and potato starch; celluloses including cellulose, methylcellulose, sodium carboxymethyl-cellulose and hydroxypropylmethyl-cellulose; and fillers including gelatin and polyvinylpyrrolidone. In addition, optionally, crosslinked polyvinylpyrrolidone, agar, alginic acid, or sodium alginate may be added as a disintegrant. In addition, the pharmaceutical composition of the present invention may further comprise anti-aggregating agents, lubricants, wetting agents, flavoring agents, emulsifying agents, and preservatives.

The preparation for parenteral administration may be formulated into the form of injections, creams, lotions, external ointments, oils, moisturizers, gels, aerosols and nasal inhalers by methods known in the art. These formulations are described in the literature (Remington's Pharmaceutical Science, 19th ed., Mack Publishing Company, Easton, Pa., 1995), which is a commonly known formulary for the entire fields of pharmaceutical chemistry.

The total effective amount of the composition of the present invention may be administered to a patient in a single dose and may be administered by a fractionated treatment protocol for a long term with multiple doses. The pharmaceutical composition of the present invention may vary in the content of the active ingredient depending on the severity of the disease. Preferably, the preferred total dosage of the pharmaceutical composition of the present invention is from about 0.01 µg to about 10,000 mg, most preferably from 0.1 µg to 500 mg (TFG 100 nM=134.33 µg/kg, TFMG 100 nM=137.015 µg/kg) per 1 kg patient weight per day. However, regarding the dosage of the pharmaceutical composition, the effective dosage for each patient is determined upon considering various factors such as formulation method, administration route and frequency of treatment, as well as the patient's age, weight, health condition, sex, severity of disease, diet and excretion rate. Therefore, one of ordinary skill in the art will be able to determine the appropriate effective dose of the composition of the present invention. The pharmaceutical composition according to the present invention is not particularly limited to the type of formulation, administration route and administration method as long as the effect of the present invention is exhibited.

As used herein, the inflammatory disease is selected from the group consisting of inflammatory bowel disease, diabetic eye disease, peritonitis, osteomyelitis, cellulitis, meningitis, encephalitis, pancreatitis, traumatic shock, bronchial asthma, rhinitis, sinusitis, otitis, pneumonia, gastritis, enteritis, cystic fibrosis, apoplexy. bronchitis, bronchiolitis, hepatitis, nephritis, arthritis, gout, spondylitis, Reiter's syndrome, polyarteritis nodosa, irritable vasculitis, Lou Gehrig's granulomatosis, Polymyalgia rheumatica, arthritic arteritis, calcium crystal arthropathies, pseudogout, non-articular rheumatism, bursitis, tenosynovitis, epicondylitis (tennis elbow), neuropathic joint disease (Charcot's joint), hemarthrosis, Henoch-Schonlein purpura, hypertrophic osteoarthropathy, multicentric reticulohistiocytoma, surcoilosis, hemochromatosis, sickle cell disease and other hemochromatosis, hyperlipoproteinemia, hypogammaglobulinemia, hyperparathyroidism, acromegaly, familial Mediterranean fever, Behcet's disease, systemic lupus erythematosus, relapsing fever, psoriasis, multiple sclerosis, sepsis, septic shock, acute respiratory distress syndrome, multiple organ dysfunction syndrome, chronic obstructive pulmonary disease, acute lung injury and broncho-pulmonary dysplasia. Preferably, the inflammatory disease may be sepsis.

The inventors have experimentally confirmed the effectiveness of the fusion polypeptides according to the present invention in the treatment of the above described inflammatory diseases, particularly sepsis.

Activated protein C (APC) used as a therapeutic agent for sepsis has characteristics of the prevention of blood clotting, anti-inflammation, protective barrier, and fibrous properties, and was approved by the FDA in 2001 and the EMA in 2002 for treating septic shock and severe asthma. In October 2011, APC was withdrawn from the market due to its lack of favorable effects of 28-day death and adverse side effects in the PROWESS and PROWESS-SHOCK tests. The most common side effects associated with APC are hemorrhage caused by degradation of procoagulant elements Va and VIIIa, which is consistent with the antithrombotic activity of APC. Therefore, there is currently no effective preventive or therapeutic method for severe sepsis.

Meanwhile, the activity of APC is caused by the interaction between the endothelial protein C receptor (EPCR) and the γ-carboxyglutamic acid (Gla) domain of PC/APC. The γ-carboxyglutamic acid (Gla) domain (PC-Gla) of PC/APC does not degrade the clotting factor, but may provide a protease capable of binding to protease-activated receptor-1 (PAR-1). When PC-Gla binds to EPCR, PAR-1 is cleaved. As a result, cell protective signaling responses such as barrier protection and anti-inflammation can be triggered.

Thrombin may bind to PAR-1 in at least three ways with a higher efficient scale of catalyst than APCs. The activity of PAR-1 by the thrombin receptor agonist peptide (TRAP) mimics the effect of thrombin in human endothelial cells. Conventional studies show that when PC binds to EPCR, PAR-1 dependent signaling by thrombin or TRAP is converted to a cytoprotective response from the pro-inflammatory signal of endothelial cells (Blood 2007, 110, 3909, Thromb Haemost 2008, 100, 101). This indicates the recruitment of PAR-1 by the use of EPCR during the cell protection.

In sum, the present inventors hypothesized that it would be possible to maximize a therapeutic effect for sepsis without causing problems such as bleeding if EPCR and PAR-1 can be simultaneously targeted by fusing a ligand capable of binding specifically to EPCR and PAR-1 through a single drug delivery system. TRAP, a peptide that activates PAR-1, was fused to the N-terminus of the human-derived ferritin monomer fragment. At the same time, a fusion polypeptide (TFG) in which PC-Gla, a peptide targeting EPCR, was fused to the C-terminus of the ferritin monomer was prepared so that the TRAP and the PC-Gla protruded outside the ferritin cage (See Example 1).

In order to prevent the effect of mutual interference between TRAP and PC-Gla fused to the N-terminus or C-terminus of the human ferritin monomer on their physiological activities, respectively, a fusion polypeptide (TFMG) was prepared in which a linker having an amino acid sequence capable of being cleaved by MMP-2 was bound between the C-terminus of the human ferritin monomer fragment and PC-Gla. The linker was cleaved at the MMP-activated pathological site, resulting in the release of PC-Gla from the ferritin cage (See Example 1).

According to another Example of the present invention, it was confirmed that MMP-2 was secreted from HUVEC cells by LPS or CLP, and that the linker in TFMG was cleaved by MMP-2 and PC-Gla was continuously released (See Example 2). Thus, it was confirmed that, when an anti-inflammatory polypeptide is fused through a linker containing an amino acid sequence capable of serving as a substrate for MMP at the C-terminus of the monomer fragment of human ferritin, the linker is exposed to MMP even after the ferritin cage is formed and thus can be cleaved by MMP to release the fused polypeptide into the pathological site.

In another Example of the present invention, the degree of binding affinity between the TFG or TFMG fusion polypeptide with EPCR was evaluated. As a result, it was observed that TFG and TFMG bind to EPCR with the same degree of binding affinity as that of PC-Gla, respectively, verifying that PC-Gla may easily bind to EPCR and exhibit its physiological activity even after PC-Gla is fused to the monomer fragment of human ferritin (See Example 3).

Further, in still another Example of the present invention, it was evaluated whether the TFG or TFMG fusion polypeptide may activate PAR-1. As a result, it was found that the TFG and TFMG fusion polypeptide activate PAR-1 to the same extent as TRAP peptide does, confirming that TRAP maintains its physiological activity of activating PAR-1 even after it was fused to the monomer fragment of human ferritin (See Example 3).

In another Example of the present invention, therapeutic effects for sepsis were evaluated after administering TFG, TFMG, or a combination of PC-GLA and TRAP to an animal model of sepsis induced by CLP, respectively. As a result, it was confirmed that TFMG- or TFG-treated groups showed remarkably excellent effects in preventing and treating sepsis in comparison with the co-administration of PC-GLA and TRAP-treated group, in terms of such evaluation factors as animal mortality, the degree of penetration of inflammatory cells into tissues, the degree of lung tissue necrosis, liver toxicity, kidney toxicity, LDH levels as an indicator of tissue damage, the secretion level of inflammatory cytokines, and the expression level of the adhesion factors of endothelial cells which promote the collapse of blood vessel barriers and the migration of leukocytes (See Example 4).

Another embodiment of the present invention provides a pharmaceutical composition comprising the fusion polypeptide which is effective in inhibiting the production of inflammation inducing mediators including TNF-α, IL-6 and IL-10.

Still another embodiment of the present invention provides use of the fusion polypeptide for preparing an agent for treating an inflammatory disease.

Another embodiment of the present invention provides a method for treating an inflammatory disease in a subject in need thereof, the method comprising administering an effective amount of a composition comprising the fusion polypeptide as an active ingredient to a subject in need thereof.

Still another embodiment of the present invention provides a method for treating an inflammatory disease in a subject in need thereof, the method comprising administering an effective amount of a composition consisting of the fusion polypeptide as an active ingredient to a subject in need thereof.

Still another embodiment of the present invention provides a method for treating an inflammatory disease in a subject in need thereof, the method comprising administering an effective amount of a composition consisting essentially of the fusion polypeptide as an active ingredient to a subject in need thereof.

As used herein, the "effective amount" of the present invention refers to an amount that, when administered to a subject, elicits an improvement, treatment, prevention, detection, or diagnostic effect of an inflammatory disease. Preferably, the term "subject" may be an animal including a mammal, particularly a human, and may include an animal-derived cells, tissues, and organs. The subject may be a patient requiring treatment.

The term "treatment" or "treating" of the present invention broadly refers to ameliorating an inflammatory disease or the symptoms of an inflammatory disease, including curing, substantially preventing and improving the conditions of such a disease. It includes, but is not limited to, ameliorating, curing or preventing one or most of the symptoms resulting from an inflammatory disease.

As used herein, the term "comprising" is used synonymously with the terms "containing" and "characterized by" and does not exclude additional components or method steps which are not mentioned in a composition or method. The term "consisting of" means to exclude additional elements, steps or components which are not mentioned. The term "consisting essentially of" means to include a material or step that does not substantially affect the basic characteristics of a composition or method, as well as the mentioned material or step.

Advantageous Effect

As described above, there is provided a fusion polypeptide, in which an anti-inflammatory polypeptide is fused to a N-terminus and/or a C-terminus of a human-derived ferritin monomer fragment having an amino acid sequence of SEQ ID NO: 1, may fuse two types of anti-inflammatory polypeptides which act through different mechanisms, respectively, into a nanocage for administration, thus the fusion polypeptide exhibiting an excellent effect in the treatment of an inflammatory disease including sepsis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 18B: TNF-a).

MODE FOR CARRYING OUT INVENTION

Figure 1A:
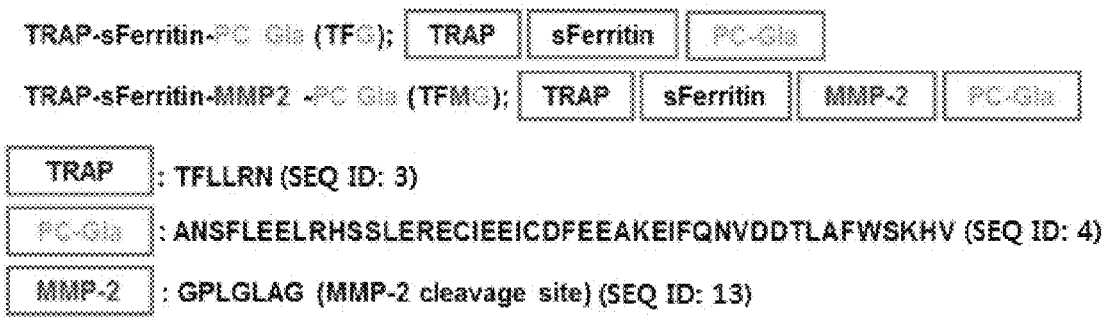
FIG. 1A and FIG. 1B are schematic diagrams showing the fusion of TFG and TFMG fusion polypeptides (FIG. 1A: Fusion schematic diagram of TFG and TFMG, FIG. 1B: 3D schematic diagram of fusion polypeptide and ferritin nanocage).

Hereinafter, the present invention will be described in detail.

However, the following Examples are merely illustrative of the present invention, while the scope of the present invention is not limited to the following Examples.

<Experimental Method>
1. Preparation of Reagents

PC-Gla and TRAP were synthesized by Peptron Inc. (Daejeon, Republic of Korea) and Anygen Inc. (Gwangju, Republic of Korea). Peptides were labeled with FNG-456 NHS ester or FNI-675 NHS ester fluorescent dyes (Bioacts Inc., Incheon, Republic of Korea). Bacterial lipopolysaccharide (LPS, serotype: 0111:B4, L5293), antibiotics (penicillin G and streptomycin), α-cyano-4-hydroxycinnamic acid (CHCA), sinapic acid, and p-aminophenylmercuric acetate were purchased from Sigma (St. Louis, Mo.). Anti-MMP-2 antibody (MAB13434) was purchased from Millipore, anti-mouse CD31 (553369) from BD Falcon, and anti-EPCR antibody (FL-238, sc-28978) from Santa Cruz.

2. Expression and Purification of TFG (TRAP-Ferritin Monomer Fragment-PC-Gla Fusion Polypeptide) and TFMG (TRAP-Ferritin Monomer Fragment-Linker-PC-Gla Fusion Polypeptide)

A plasmid was constructed for the expression of short ferritin (sFn) by deleting the short E-helix from ferritin light chain. The DNA plasmids of TFG and TFMG were constructed by introducing TRAP (TFLLRN)(SEQ ID NO: 3) peptide sequence into the N-terminus of sFn with restriction sites, SpeI and XhoI, at 5'- and 3'-ends. In addition, the PC-Gla domain (ANSFLEELRHSSLERECIEEICDFEE-AKEIFQNVDDTLAFWSKHV)(SEQ ID NO: 4) sequence or MMP-2 cleavage site (GPLGLAG)(SEQ ID NO: 13) were constructed in front of the PC-Gla domain to the C-terminus of sFn at 5'- and 3'-ends with restriction sites, SpeI and XhoI at 5'- and 3'-ends. Primers were designed as follows: (+) 5' CAC TTT TCT TCT TCG GAA CG 3'(SEQ ID NO: 16) and (−) 5' CTA GCG TTC CGA AGA AGA AAA GTG GTA C 3'(SEQ ID NO: 17) for TRAP; (+) 5' GAA ACT AGT GCC AAC TCC TTC CTG GAG G 3'(SEQ ID NO: 18) and (−) 5' GAA CTC GAG GAC GTG CTT GGA CCA G 3'(SEQ ID NO: 19) for PC-Gla domain; (+) 5' GAA ACT AGT GGT CCT CTA GGT CTA GCC GGT GCC AAC TCC TTC CTG G 3'(SEQ ID NO: 20) and (−) 5' GAA CTC GAG GAC GTG CTT GGA CCA G 3' (SEQ ID NO: 21) for the MMP-2 cleavage site in front of the PC-Gla domain. TFG and TMFG plasmids were transformed into *Escherichia coli* (*E. coli*) expression strain BL21 (DE3). Cells were grown at 37° C. in LB medium containing 50 μg/ml kanamycin until $OD_{600}$ reached 0.5, and the expression of protein was induced by 0.1 M IPTG treatment at 37° C. for 5 hours. After induction, cells were harvested by centrifugation, and the pellets were suspended in lysis buffer (20 mM Tris-HCl pH 8.0, 100 mM NaCl, 1% Triton X-100, 1 mM PMSF, 1 mM DTT 1:000 dilution protease inhibitor cocktail) and homogenized with an ultrasonic processor. The inclusion bodies from cell lysates were solubilized by incubating in binding buffer (20 mM Tris-HCl pH 8.0, 300 mM NaCl, 10 mM imidazole) containing 8 M urea at room temperature for 1 hour. Subsequently, the denatured protein was loaded onto a nickel ion chelate affinity column rinsed with a washing buffer (20 mM Tris-HCl pH 8.0, 500 mM NaCl, 30 mM imidazole) containing 8 M urea. The protein was eluted with elution buffer (20 mM Tris-HCl pH 8.0, 100 mM NaCl, 300 mM imidazole) and refolded by dialysis with a gradient of urea.

3. Characterization of TFMG and TFG

The mass spectrum of each construct monomer was confirmed by matrix assisted laser desorption ionization time of flight (MALDI-ToF). MALDI-ToF MS was carried out using a Bruker Daltonics Microflex MALDI-ToF mass spectrometer (Bremen, Germany) with a 337 nm nitrogen laser. Mass spectra were obtained in the linear and positive-ion mode with an acceleration voltage of 20 kV. A saturated solution of cyano-4-hydroxycinnamic acid (CHCA) or sinapic acid in 50% acetonitrile, containing a final concentration of 0.1% trifluoroacetic acid, was used as the matrix solution. A CHCA matrix was chosen for analysis of fragments after enzyme digestion or sinapic acid for intact proteins. The analyte-matrix solution was prepared at a ratio of 1:2 (analyte:matrix, v/v). Each mixture was thoroughly mixed, and 1 μL of the analyte-matrix solution was deposited onto the sample plate and dried by vacuum evaporation. The spectrometer was calibrated using bradykinin; cytochrome C and bovine serum albumin were run as close external standards. Transmission electron microscopy (TEM) images were recorded using an FEI Tecnai (Korea Basic Science Institute, KBSI). The size of nanocaged TFG and TFMG was measured using a DelsaMax Pro light scattering analyzer (Beckman Coulter).

4. Cell Culture

The primary HUVECs were obtained from Cambrex BioScience (Charles City, Iowa) and maintained as previously described. All experiments were performed using HUVECs at passage 3-5. Human neutrophils were freshly isolated from whole blood (15 ml) obtained by venous venipuncture from five healthy volunteers, and maintained as previously described.

5. Animal Care

Male C57BL/6 mice (6-7 weeks of age, 18-20 g) were purchased from Orient Biotech (Seongnam, Gyeonggi Province, Republic of Korea) and used after 12 days of acclimation. Five mice per cage were housed under the conditions of a controlled temperature (20-25° C.), humidity (40-45%), and 12:12 h day/night cycle, while being fed with a normal rodent pellet and water ad libitum. All animals were treated according to the Guidelines for the Care and Use of Laboratory Animals issued by Kyungpook National University.

6. Preparation of Cecal Ligation and Puncture (CLP) Sepsis Animal Models

To induce inflammation, male mice were anesthetized with 2% isoflurane (JW Pharmaceutical, Republic of Korea) in oxygen delivered via a small rodent gas anesthesia machine (RC2, Vetequip, Pleasanton, Calif.), first in a breathing chamber and then via a facemask. They were allowed to breathe spontaneously during this procedure. The CLP-induced inflammation model was prepared as previously described. In brief, a 2-cm midline incision was made to expose the cecum and adjoining intestine. The cecum was then tightly ligated with a 3.0-silk suture at 5.0 mm from the cecal tip and punctured once using a 22-gauge needle for the induction of high grade inflammation. It was then squeezed gently to extrude a small amount of feces from the perforation site and returned to the peritoneal cavity. The laparotomy site was then sutured with 4.0-silk. In sham control animals, the cecum was exposed but not ligated or punctured and then returned to the abdominal cavity. This protocol was approved by the Animal Care Committee at Kyungpook National University prior to the conduct of the study (IRP No, KNU 2012-13).

7. Gelatin Zymography

The activity of MMP-2 and MMP-9 enzymes in medium and plasma was determined by SDS-PAGE gelatin zymography. Gelatinases present in the plasma degrade the gelatin matrix, leaving a clear band after staining the gel for protein. Briefly, LPS time-dependently treated HUVECs media and albumin-derived septic mice plasma (normalized to an equal amount of protein [20 μg]) were denatured in the absence of a reducing agent and electrophoresed using 10% SDS-PAGE containing 0.1% (w/v) gelatin. Gels were incubated in the presence of 2.5% Triton X-100 at room temperature for 2 h and subsequently at 37° C. overnight in a buffer containing 10 mM $CaCl_2$, 0.15M NaCl, and 50 mM Tris (pH 7.5). Thereafter, gels were stained with 0.25% Coomassie Blue, and proteolysis was detected as a white band against a blue background.

8. Cleavage of Nanocaged TFMG by MMP-2

To evaluate whether TFMG could be selectively cleaved by MMP2, TFMG was incubated with APMA-mediated activated MMP-2 in PBS at 37° C. for 3 h. The cleaved fragments of TFMG were detected by MALDI-ToF.

9. Enzyme-Linked Immunosorbent Assays (ELISA) for Evaluating EPCR (Endothelial Protein C Receptor) Binding Affinity To evaluate the interaction of the wild-type PC, PC-Gla peptides, TFG, and TFMG with EPCR, 96-well flat microtiter plates were coated with soluble EPCR in 20 mM carbonate-bicarbonate buffer (pH 9.6) containing 0.02% sodium azide, overnight at 4° C. After the plates were washed three times in TBS buffer (0.1 M NaCl, 0.02 M Tris-HCl, pH 7.4) containing 0.05% Tween 20, the plates were incubated with wild-type PC, PC-Gla peptides, TFG, and TFMG (7-1000 nM) diluted in the buffer for 1 h. After the plates were rinsed again, they were incubated with a goat anti-protein C polyclonal antibody (1:1000) for 1 h. Then, the plates were washed and incubated with rabbit anti-goat IgG (KPL, MD, 1:1000) for 1 h. After washing, the plates were incubated with 2,2'-azino-di(3-ethylbenzthiazoline-6-sulfonate) (ABTS; KPL, Gaithersburg, Md.). Colorimetric analysis was performed by measuring absorbance values at 405 nm.

10. Isolation of Endothelial Cells from Mouse

The endothelial cells were isolated according to the manufacturer's (Dynal Biotec, Lake Success, N.Y.) instructions, using Dynabeads coupled to anti-CD31 antibody and the Dynal Magnetic holder. Briefly, for endothelial cell isolation, four to six mice (6-10 weeks old) were anesthetized, followed by exposure of the peritoneal cavity. Excised lungs and hearts were put into RPMI media, followed by removing other tissues from the heart and lungs, and then rinsing once in PBS. The lungs and heart were incubated with 1.0 mg/mL of collagenase A in a 50 mL tube for 1 h at around 37° C. Every 5 min during this incubation, the tube was gently agitated for a few seconds, and then the suspension was transferred into a new 50 mL tube by passing it through the 70 um tissue sieve (BD Falcon). The filtered cell suspension was centrifuged for 10 min at 1000 rpm. After removal of the supernatant, the cell pellet was washed once with cold PBS in a new 15-mL tube. To prepare the Dynabead-coupled anti-mouse CD31 antibody, Dynabeads (60 µl) were washed with MACS buffer (PBS, 0.5% BSA, 2 mM EDTA) on a magnetic holder (Invitrogen). The Dynabeads were resuspended with MACS buffer (600 al), anti-mouse CD31 (5 µg of per 10 µl of beads) was added, and the mixture was incubated for 12 h at 4° C. Cells were incubated with Dynabead-coupled anti-mouse CD31 antibody for 10 min at room temperature and then placed in a magnetic holder. Cell suspension was slowly added to a 15-mL tube by placing the pipette on the wall of the tube. After incubation for 5 min, PBS was carefully removed by aspiration. The Dynabead-coupled anti-mouse CD31 antibodies were washed three times in cold PBS, the pellet was resuspended in EBM-2 growth medium, and then harvested and lysed in RIPA buffer containing protease inhibitor cocktail on ice.

11. Fluorescence of PC-Gla Domain, TFG, and TFMG

PC-Gla, TFG, and TFMG were labeled with FNG-456 NHS ester for in vitro assays or FNI-675 NHS ester for in vivo assays at a molar ratio of 1:3. Briefly, each molecule (10 µM) was dissolved in PBS (1.5 mL), and FNG-456 NHS ester (30 µM) or FNI-675 NHS ester (30 µM) was dissolved in DMSO (0.2 mL). Each molecule and fluorescent dye was reacted at room temperature for 3 h. The reaction product was passed through a 0.2-µm filtering unit, and the unreacted dye was separated on a PD midiTrap™ G-25 (GE Healthcare, UK) that had been pre-equilibrated in PBS with 2 mM sodium azide. This process yielded more than 2.17 µM of each nanoparticle with more than 1.5 ratio of dye per protein.

12. HUVEC Cell-Binding Assay

A direct cell-binding assay was performed on HUVECs and in vivo using fluorescence labeled-PC-Gla, TFG, and TFMG. The assay was performed with PC-Gla, TFG, or TFMG treated on HUVECs, intravenously injected mice, and isolated mouse endothelial cells. The fluorescence value of the HUVECs or endothelial cells were measured with tightly bound PC-Gla, TFG, and TFMG, respectively. The concentrations of PC-Gla, TFG, and TFMG were measured by using the nanoparticle ratio of fluorescent dye per protein.

13. PAR-1 Cleavage Assay

HUVECs at 90% confluence in 24-well plates were transiently transfected with pRc/RSV containing ALP-PAR-1-TF cDNA in antibiotic-free Opti-MEM medium using Lipofectamine (Invitrogen) according to the manufacturer's instruction. On the following day, cells were washed and incubated in serum-free medium for 5 h. Cells were then incubated for an additional hour with thrombin, TRAP, TFG, or TFMG. Conditioned medium was collected and centrifuged to remove cellular debris. Supernatant was collected, and ALP (alkaline phosphatase) activity was measured using EnzoLyte™ p-nitrophenyl phosphate alkaline phosphatase assay kit (AnaSpec, San Jose, Calif.) according to the manufacturer's instructions.

14. H&E Staining and Histopathological Examination

Male C57BL/6 mice underwent CLP and were administered PC-Gla with TRAP, TFG, or TFMG (200 nM) intravenously at 6 h after CLP (n=5). Mice were euthanized 96 h after CLP. To analyze the phenotypic change of the lungs in mice, lung samples were removed from each mouse, washed tree times in PBS (pH 7.4) to remove remaining blood, fixed in 4% formaldehyde solution (Junsei, Tokyo, Japan) in PBS, pH 7.4 for 20 h at 4° C. After fixation, the samples were dehydrated through ethanol series, embedded in paraffin, sectioned into 4-µm sections, and placed on a slide. The slides were de-paraffinized in a 60° C. oven, rehydrated, and stained with hematoxylin (Sigma). To remove over-staining, the slides were quick dipped three times in 0.3% acid alcohol, and counterstained with eosin (Sigma). They are then washed in ethanol series and xylene, and then coverslipped. Light microscopic analysis of lung specimens was performed by blinded observation to evaluate pulmonary architecture, tissue edema, and infiltration of the inflammatory cells. The results were classified into four grades where Grade 1 represented normal histopathology; Grade 2 represented minimal neutrophil leukocyte infiltration; Grade 3 represented moderate neutrophil leukocyte infiltration, perivascular edema formation, and partial destruction of pulmonary architecture; and Grade 4 included dense neutrophil leukocyte infiltration, abscess formation, and complete destruction of pulmonary architecture.

15. Immunofluorescence Staining

HUVECs were grown to confluence on glass cover slips coated with 0.05% poly-L-lysine in complete media containing 10% FBS and maintained for 48 h. Cells were then stimulated with LPS (100 µg/ml) for 6 h, followed by treatment with PC-Gla with TRAP, TFG, or TFMG for 6 h. For cytoskeletal staining, the cells were fixed in 4% formaldehyde in TBS (v/v) for 15 min at room temperature, permeabilized in 0.05% Triton X-100 in TBS for 15 min, and blocked in blocking buffer (5% bovine serum albumin (BSA) in TBS) overnight at 4° C. Then, the cells were incubated with a rabbit anti-EPCR polyclonal antibody (Santa Cruz, Calif.). EPCR was visualized using an Alexa Fluor® 647-conjugated secondary antibody (Molecular Probes, donkey anti-rabbit IgG) and observed by confocal microscopy at a magnification of 630× (TCS-Sp5, Leica Microsystems, Germany).

16. Histological Analysis of EPCR Binding In Vivo

Twenty-four hours prior to CLP surgery, fluorescence labeled-PC-Gla, TFG, and TFMG (200 nM/mouse) was intravenously injected into the mice, respectively. After 24 h, mouse vena cava was enucleated and fixed in visikol for 24 h. Subsequently, vena cava was embedded in optimum cutting temperature (OCT) compound (Tissue Tek) at −80° C. Consecutive sections were incubated with anti-EPCR antibody (Santa Cruz, Calif.), anti-rabbit Alexa 488 (green), anti-CD31 antibody, and anti-rabbit Alexa 350 (blue), and observed by confocal microscopy at 63× magnification (TCS-SP5, Leica microsystem, Germany).

17. Analysis of Serum Components in Septic Animal Model

Fresh serum was used for assaying aspartate transaminase (AST), alanine transaminase (ALT), blood urea nitrogen (BUN), creatinine, and LDH using biochemical kits (Mybiosource). To determine the concentrations of IL-6, IL-10, and TNF-α, commercially available ELISA kits were used according to the manufacturer's protocol (R&D Systems). Values were measured using an ELISA plate reader (Tecan, Austria GmbH, Austria).

18. In Vitro Permeability Assay

For spectrophotometric quantification of endothelial cell permeabilities in response to increasing concentrations of each molecule, the flux of Evans blue-bound albumin across functional cell monolayers was measured using a modified 2-compartment chamber model, as previously described. HUVECs were plated ($5\times10^4$/well) in 12-mm diameter Transwells with a pore size of 3 µm for 3 days. Confluent monolayers of HUVECs were exposed to LPS (100 ng/mL) for 4 h before being subjected to PC-Gla with TRAP, TFG, or TFMG (up to 100 nM). Transwell inserts were then washed with TBS (pH 7.4), followed by the addition of Evans blue (0.5 mL; 0.67 mg/mL) diluted in a growth medium containing 4% BSA. Fresh growth medium was then added to the lower chamber, and the medium in the upper chamber was replaced with Evans blue/BSA. Ten minutes later, the optical density of the sample in the lower chamber was measured at 650 nm.

19. In Vivo Permeability and Leukocyte Migration Assays

CLP-operated mice were injected with PC-Gla with TRAP, TFG, or TFMG intravenously. After 6 h, 1% Evans blue dye solution in normal saline was injected intravenously into each mouse. Thirty minutes later, the mice were sacrificed, and the peritoneal exudates were collected after being washed with normal saline (5 mL) and centrifuged at 200×g for 10 min. The absorbance of the supernatant was read at 650 nm. The vascular permeability was expressed in terms of dye (mg/mouse), which leaked into the peritoneal cavity according to a standard curve of Evans blue dye, as previously described.

For assessment of total leukocyte migration, CLP operated mice were treated with each nanoparticle (100 nM) 6 h after CLP surgery. The mice were then sacrificed and the peritoneal cavities were washed with 5 mL of normal saline. Peritoneal fluid (20 µL) was mixed with Turk's solution (0.38 mL; 0.01% crystal violet in 3% acetic acid) and the number of leukocytes was counted under an optical microscope. The results were expressed as neutrophils×$10^6$ per peritoneal cavity.

20. Expression Analysis of Cell Adhesion Factor (CAM)

The expression of vascular cell adhesion molecule-1 (VCAM-1), intercellular adhesion molecule-1 (ICAM-1), and E-selectin on HUVECs were determined by a whole-cell ELISA as described. Briefly, confluent monolayers of HUVECs were treated with PC-Gla with TRAP, TFG, or TFMG for 6 h followed by LPS (100 ng/mL) for 16 h (VCAM-1 and ICAM-1) or 24 h (E-Selectin). After washing, mouse anti-human monoclonal VCAM-1 (100 µM; clone; 6C7.1), ICAM-1 (clone; P2A4) and E-selectin (clone; P3H3) antibodies (Millipore Corporation, 1:50 each) were added. After 1 h (37° C., 5% $CO_2$), the cells were washed three times and then 1:2000 peroxidase-conjugated anti-mouse IgG antibody (100 µl; Sigma) was added for 1 h. The cells were washed again three times and developed using the o-phenylenediamine substrate (Sigma). Colorimetric analysis was performed by measuring absorbance at 490 nm. All measurements were performed in triplicate wells.

21. Cell-Cell Adhesion Assay

Adherence of monocytes to endothelial cells was evaluated by fluorescent labeling of monocytes, as previously described. Briefly, monocytes were labeled with 5 µM Vybrant DiD for 20 min at 37° C. in phenol red-free RPMI containing 5% FBS. After washing, the cells ($1.5\times10^6$ cells/mL, 200 µL/well) were resuspended in adhesion medium (RPMI containing 2% fetal bovine serum and 20 mM HEPES). The cells were then added to confluent monolayers of HUVECs in 96-well plates. Prior to the addition of cells, HUVECs were treated PC-Gla with TRAP, TFG, or TFMG for 6 h, followed by treatment with LPS (100 ng/mL, 4 h). Quantification of cell adhesion was determined as previously described.

22. Statistical Analysis

All experiments were performed independently at least three times. Values are expressed as means±SEM. The statistical significance of differences between test groups was evaluated using SPSS for Windows, version 16.0 (SPSS, Chicago, Ill.). Statistical relevance was determined by one-way analysis of variance (ANOVA) and Tukey's post-test. P values less than 0.05 were considered to indicate a statistical significance. Survival analysis of CLP-induced sepsis was performed using Kaplan-Meier analysis.

Experimental Results

Example 1

Preparation and Characterization of Fusion Polypeptides

Figure 1B:
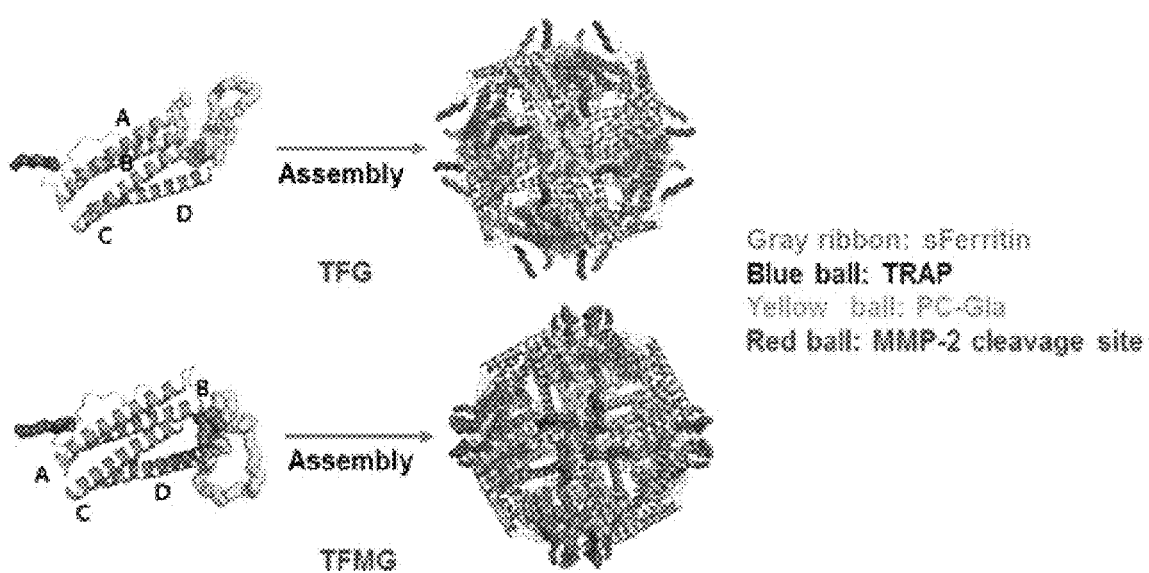

A short ferriitin (sFn) was constructed by deleting the short helix E and loop from the ferritin light chain to make genetic modification more amenable. To prepare TRAP-ferritin-PC-Gla (TFG) protein, the sFn was genetically engineered, inserting the EPCR ligand at the C-terminus and PAR-1 activator (TRAP peptide) at the N-terminus (FIG. 1A & FIG. 1B). To prevent free PC-Gla from interfering with the remaining TRAP-ferritin during simultaneous double binding to each receptor, the matrix metalloproteinase (MMP)-2 binding site was inserted between the sFn and the PC-Gla domain (TFMG) so that PC-Gla was able to be released from nanocages when they reached MMP-activating sites.

Figure 2A:
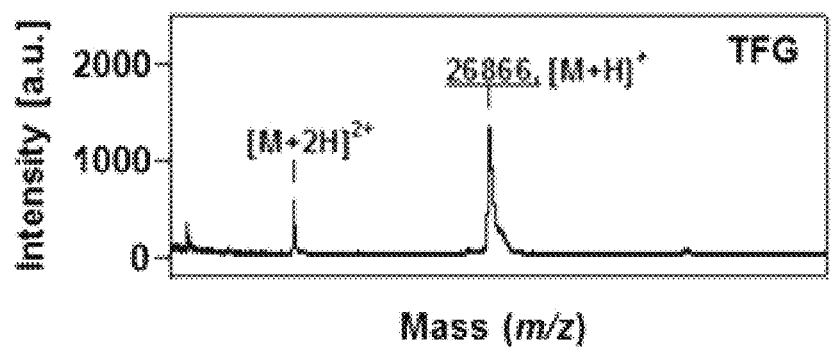
FIG. 2A and FIG. 2B show the results of measurement of the molecular weights of TFG and TFMG with a MALDI-ToF mass spectrometer (FIG. 2A: TFG, FIG. 2B: TFMG).
Figure 2B:
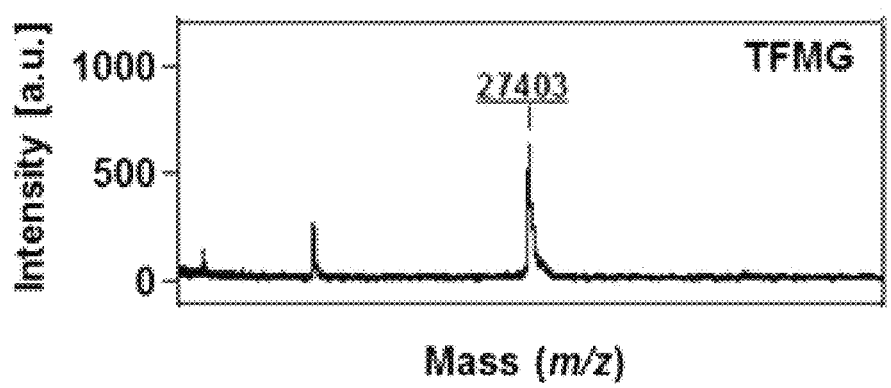
Figure 3A:
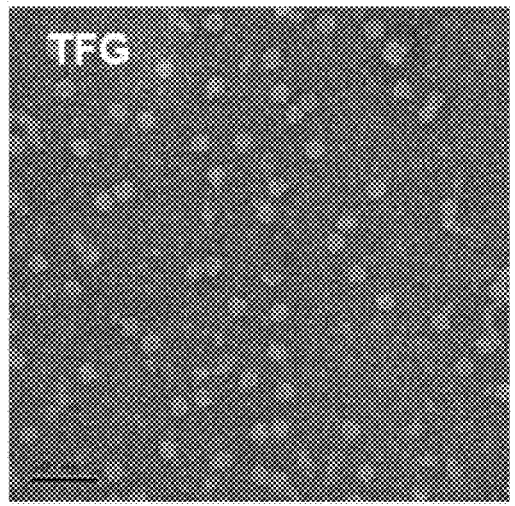
FIG. 3A and FIG. 3B are the result of TEM imaging observing that TFG and TFMG form a ferritin cage by self-assembling (FIG. 3A: TFG, FIG. 3B: TFMG).
Figure 3B:
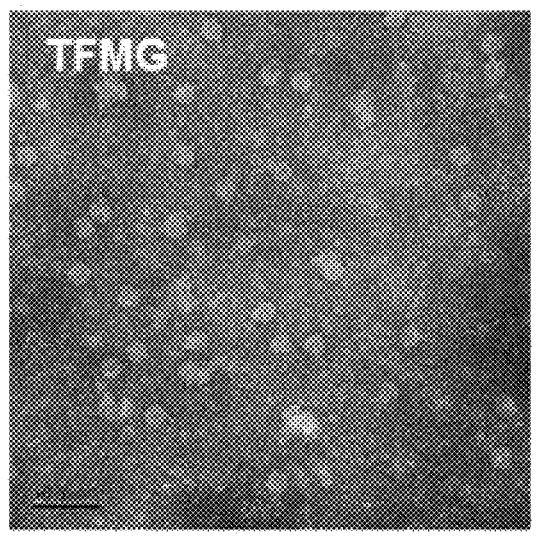
Figure 4:
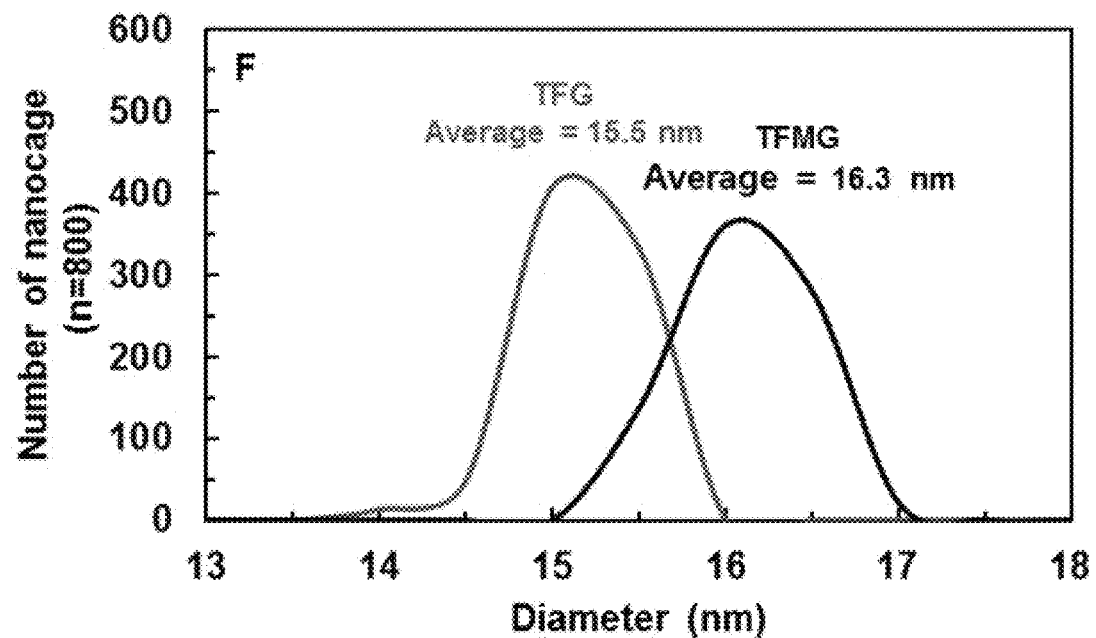
FIG. 4 shows the results of measuring the diameter of the ferritin cage formed by TFG and TFMG.

The molecular weights of purified TFG and TFMG monomers were 26,866 Da and 27,403.6 Da, respectively, as determined by the matrix-associated laser desorption ionization time-of-flight (MALDI-ToF) mass spectrometry (FIG. 2A & FIG. 2B). The lack of large aggregates in TEM images of negatively stained TFG and TFMG verifies this cage structure (FIG. 3A & FIG. 3B). The mean outer diameters of the TFG and TFMG nanocages were 15.5 nm and 16.3 nm, respectively (FIG. 4). The size distribution of each construct increased with the addition of MMP-2 binding sites between the C-terminus of sFn and the PC-Gla region.

Example 2

Linker Cleavage of TFMG by MMP-2 and Evaluation on Secretion of PC-Gla

Figure 5A:
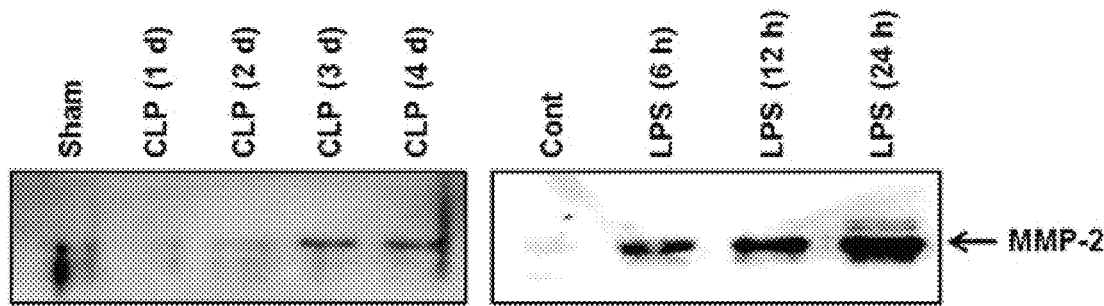
FIG. 5A and FIG. 5B show the results of secretion of MMP-2 by CLP or LPS stimulation in HUVEC cells (FIG. 5A: results of Western-blot, FIG. 5B: results of zymography).
Figure 5B:
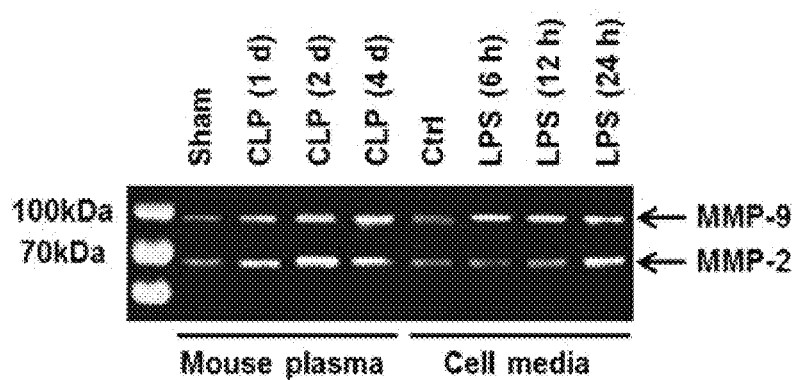
Figure 6:
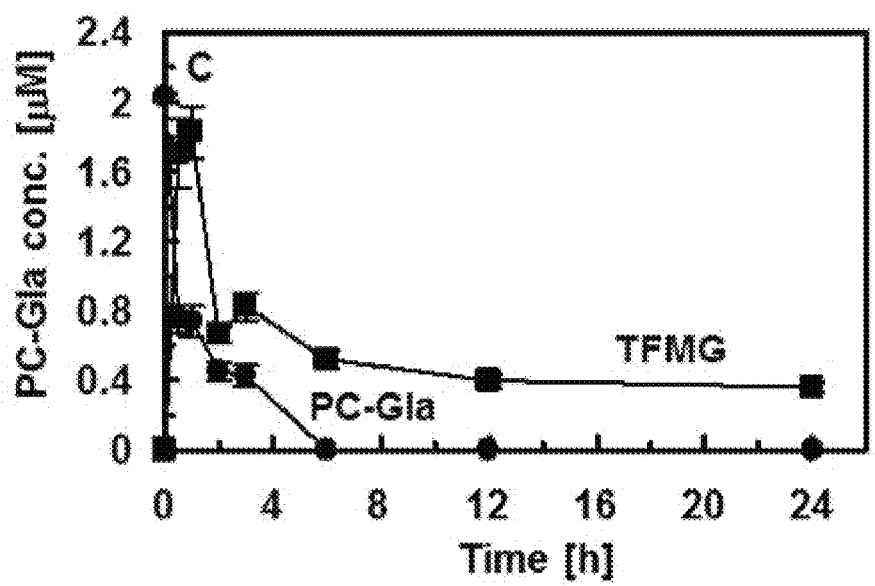
FIG. 6 shows the result of observing whether PC-Gla is released by cleavage of the linker in TFMG by AMPA-activated MMP-2.
Figure 7:
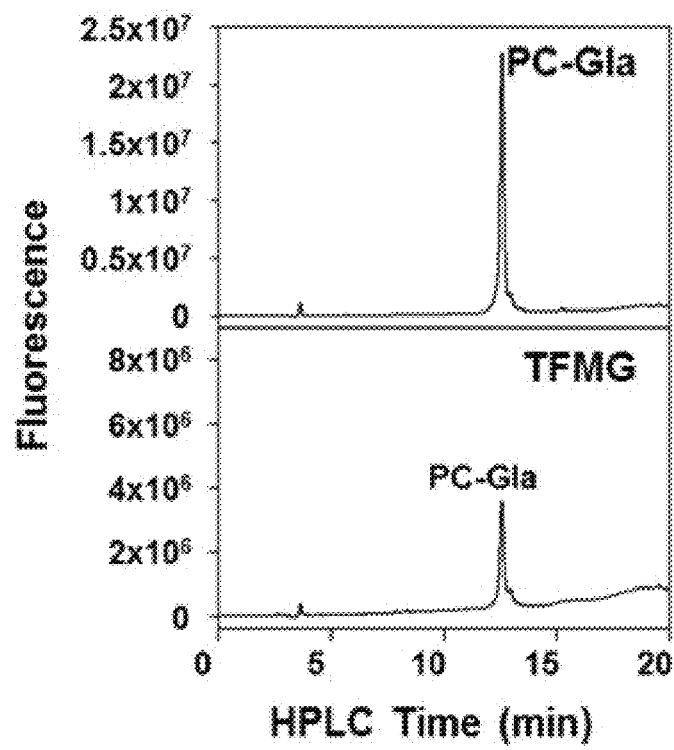
FIG. 7 shows the HPLC analysis results of confirming the released PC-Gla after the linker of TFMG was cleaved by MMP-2.
Figure 8:
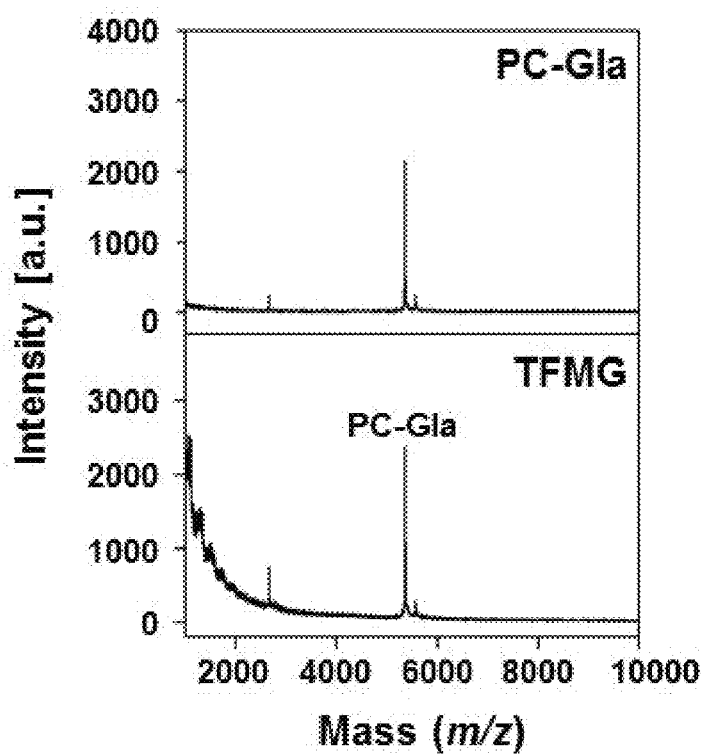
FIG. 8 shows the MALDI-ToF results of confirming the released PC-Gla after the linker of TFMG was cleaved by MMP-2.
Figure 9:
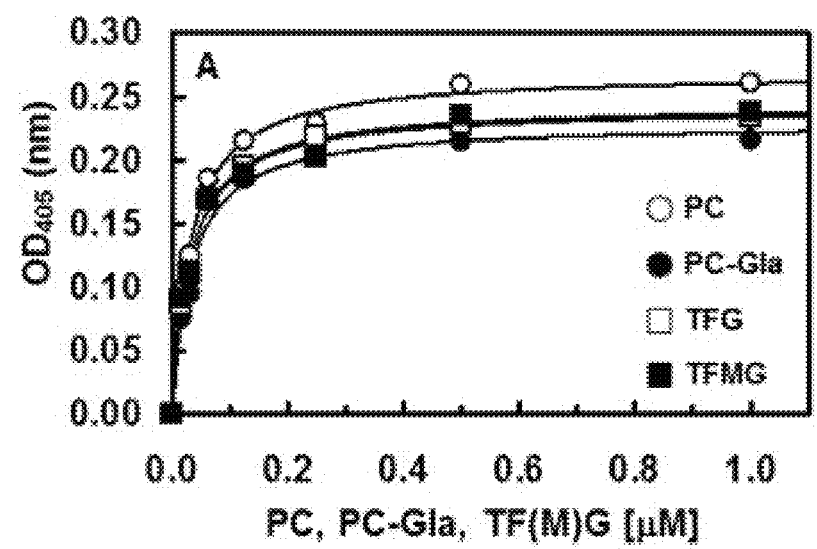
FIG. 9 shows the solid-phase ELISA results of evaluating the binding affinity of Protein C (PC), PC-Gla domain, TFG and TFMG to soluble EPCR.
Figure 10:
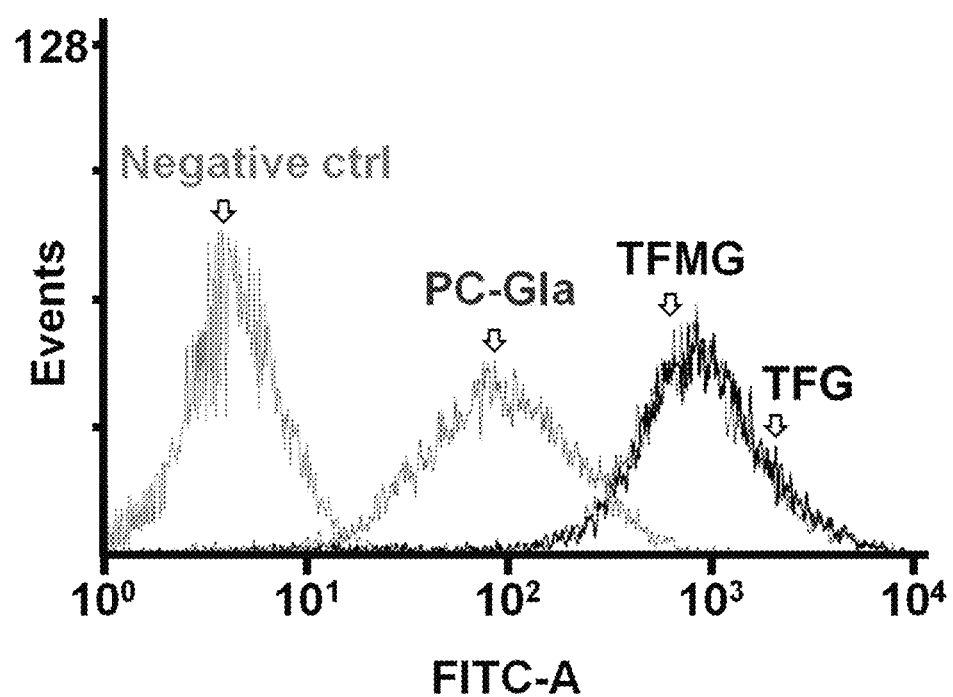
FIG. 10 shows the results of evaluating the binding affinity of PC-Gla, TFG and TFMG to HUVEC cells.
Figure 11:
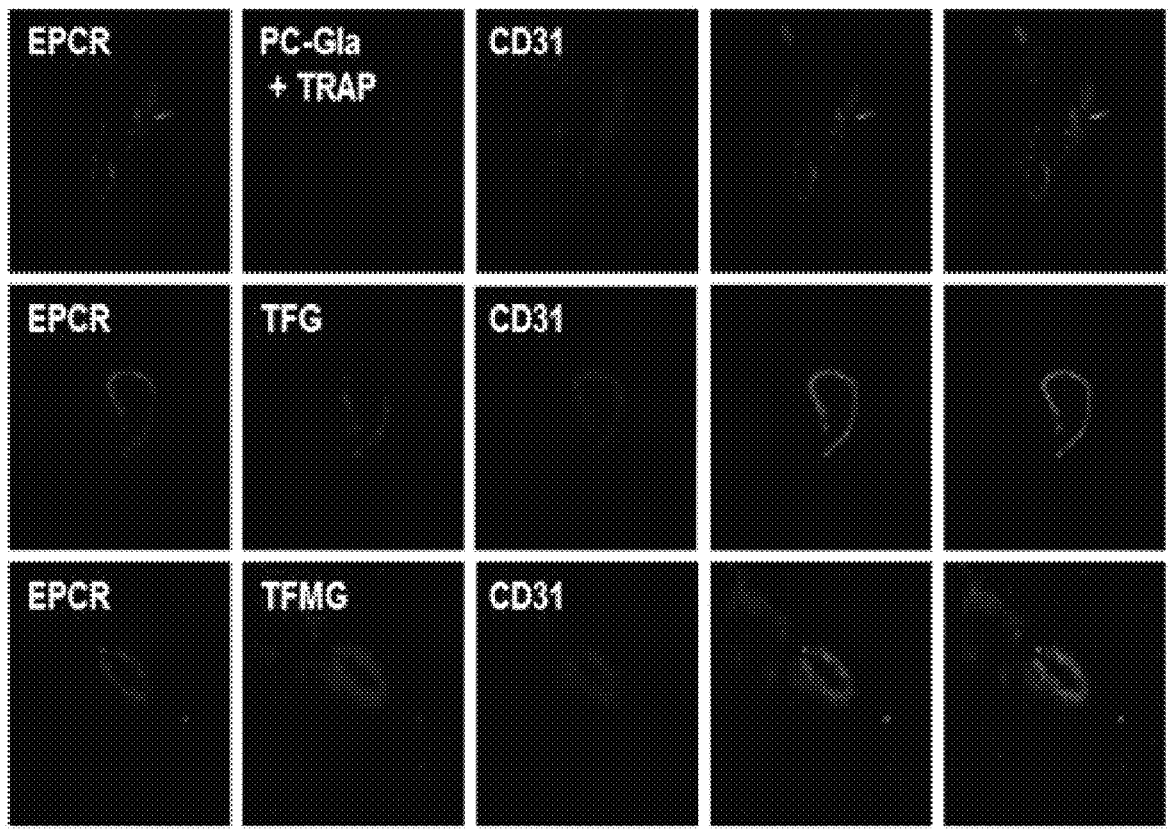
FIG. 11 shows the in vivo immunohistological staining results of confirming the binding affinity of PC-Gla, TFG and TFME, respectively.
Figure 12A:
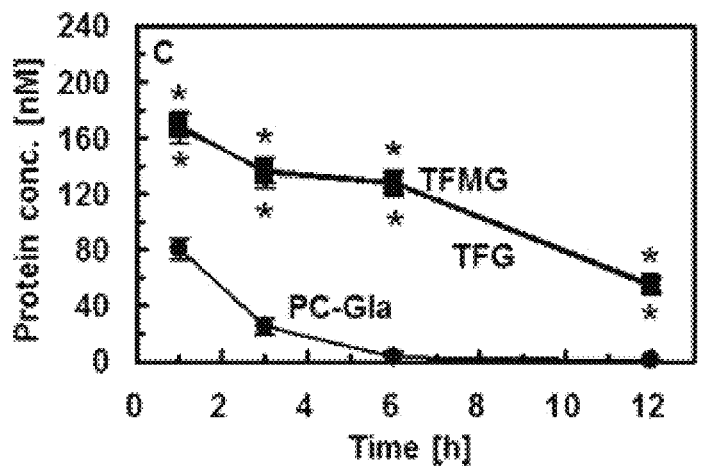
FIG. 12A and FIG. 12B show the results of evaluating the degree of binding affinity of PC-Gla, TFG and TFMG to endothelial cells in vitro (HUVEC) or in vivo (mouse animal model) (FIG. 12A: in vitro, FIG. 5B: in vivo), respectively.
Figure 12B:
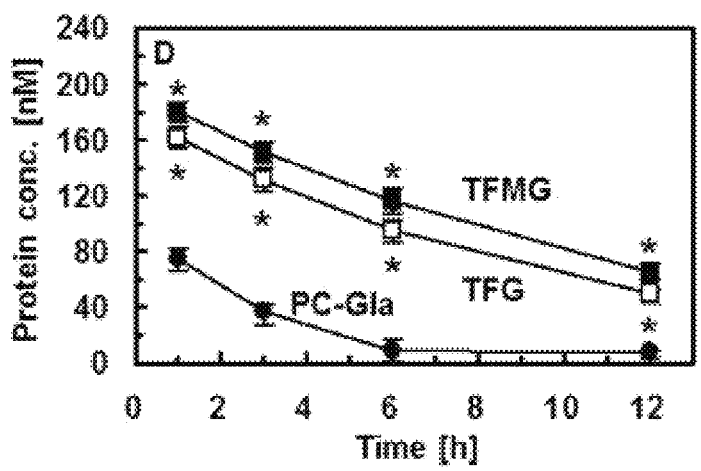
Figure 13:
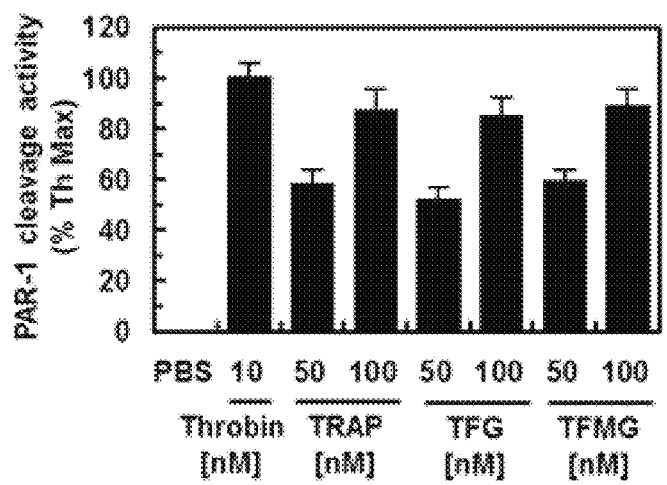
FIG. 13 shows the results of evaluating the degree of activation of PAR-1 by TRAP peptide, TFG and TFMG, respectively.
Figure 14:
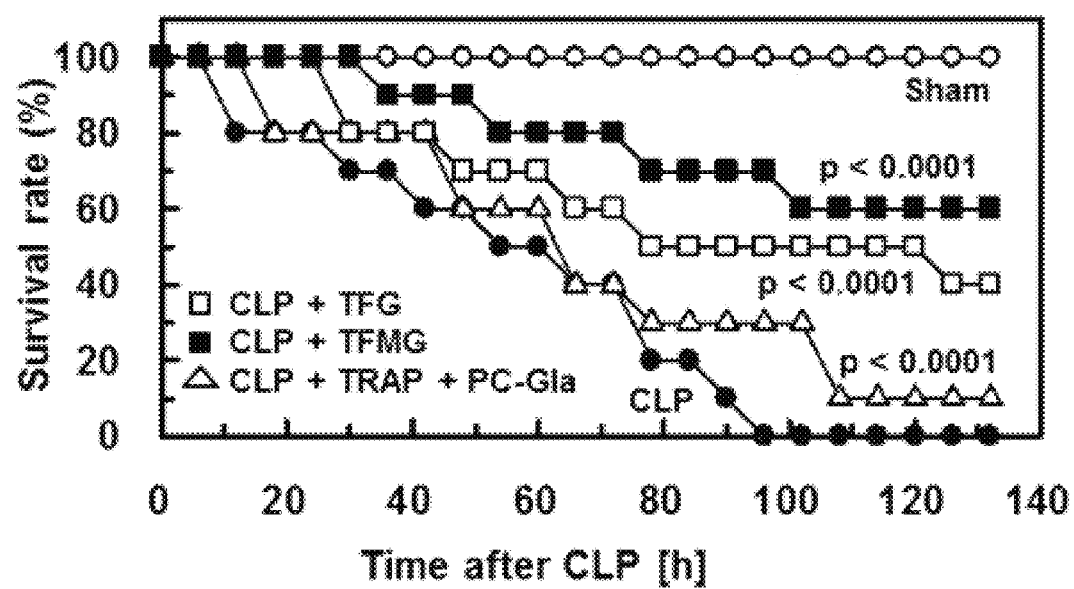
FIG. 14 shows the results of observing the survival rate of animals after TFG administration, TFMG administration, and co-administration of TRAP and PC-Gla to an animal model of CLP-induced sepsis, respectively.
Figure 15:
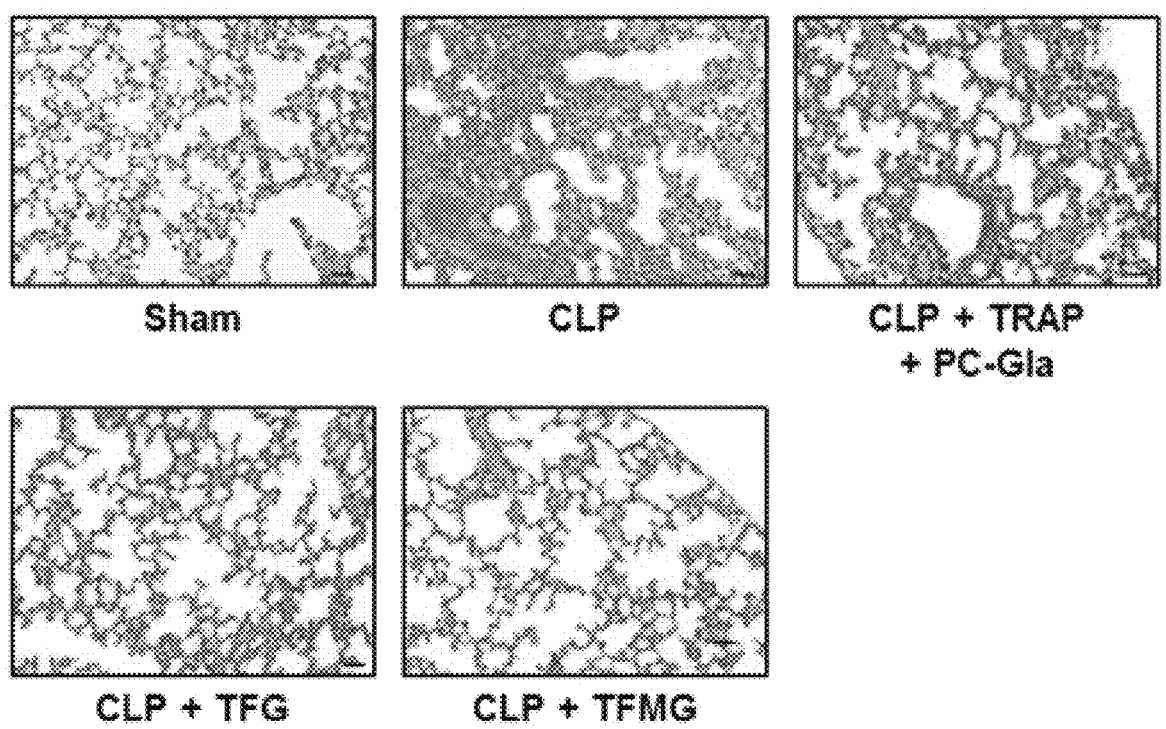
FIG. 15 shows the results of observing the infiltration of inflammatory cells into tissues and the damage of the lung tissues of the animal after TFG administration, TFMG administration, and co-administration of TRAP and PC-Gla to an animal model of CLP-induced sepsis, respectively.
Figure 16:
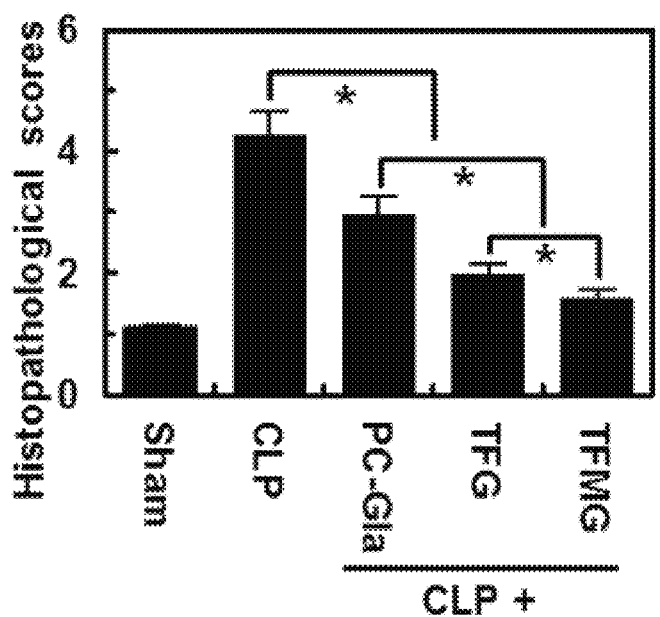
FIG. 16 shows the results of scoring the degree of lung damage in animals after TFG administration, TFMG administration, and co-administration of TRAP and PC-Gla to an animal model of CLP-induced sepsis, respectively.
Figure 17A:
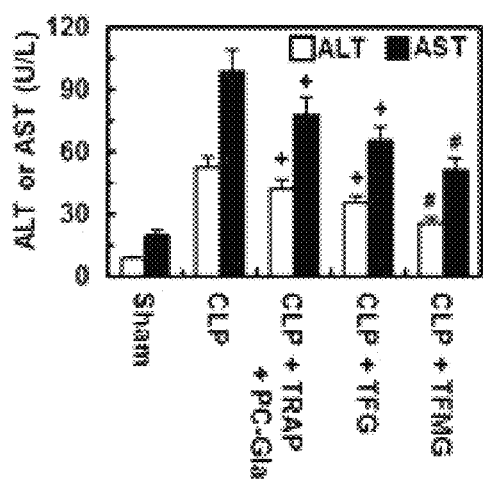
FIG. 17A, FIG. 17B, FIG. 17C and FIG. 17D show the results of the evaluating ALT or AST, creatinine, BUN and LDH levels after TFG administration, TFMG administration and co-administration of TRAP and PC-Gla to an animal model of CLP-induced sepsis, respectively.
Figure 17B:
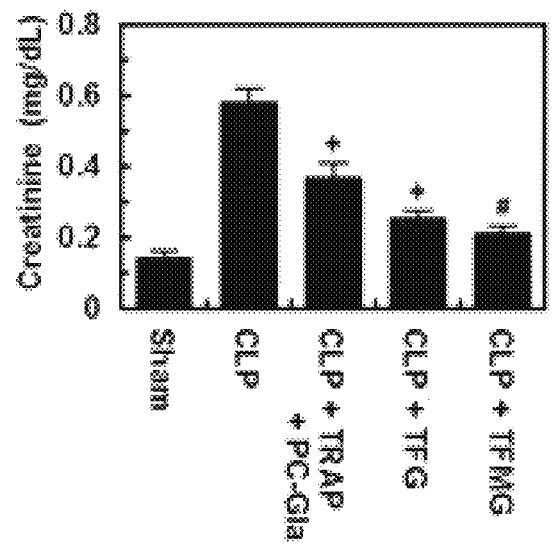
Figure 17C:
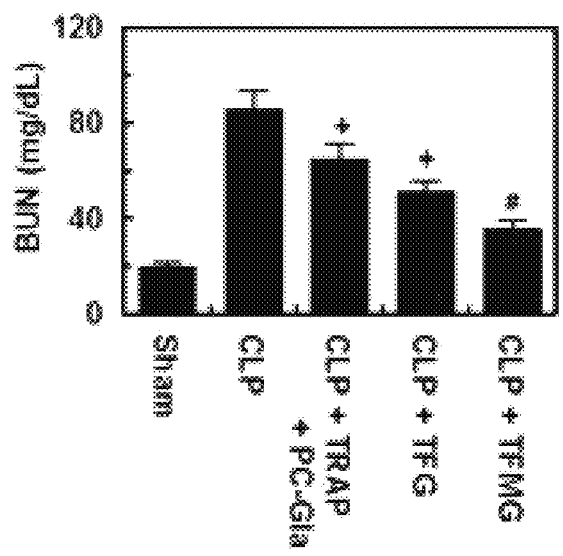
Figure 17D:
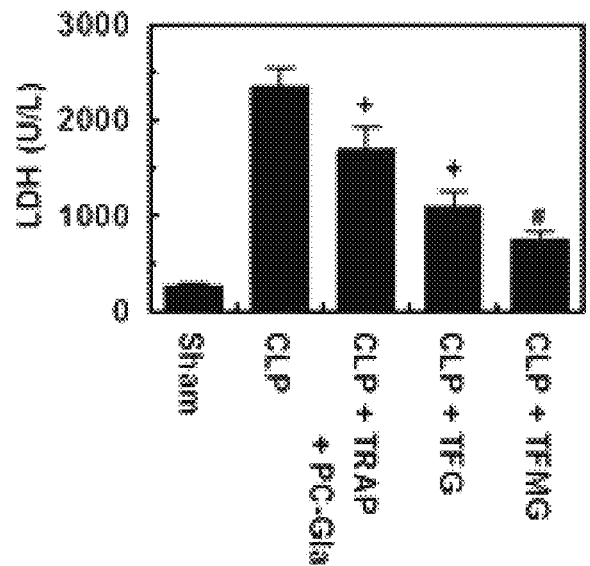

It was verified that LPS- or CLP-induced MMP-2 was released from activated HUVECs using Western blotting and zymography (FIG. 5A & FIG. 5B). To evaluate whether PC-Gla could be selectively cleaved from TFMG by MMP-2 and whether the release of PC-Gla from TFMG was regulated, TFMG was incubated with p-aminophenylmercuric acetate (AMPA)-activated MMP-2. It was found that TFMG continuously released PC-Gla (FIG. 6), TFMG was cleaved by MMP-2 to release PC-Gla in agreement with the calculated mass (5,518.6 Da by MALDI-ToF) (FIG. 7 & FIG. 8).

Example 3

Evaluation on Binding Affinity Toward EPCR and PAR-1 Cleavage Activity

In the context of the binding properties of TFG or TFMG to EPCR and PAR-1, the present inventors sought to determine whether the attachment of multiple ligands to the ferritin scaffold affects the binding dynamics in vitro or in vivo.

Figure 18A:
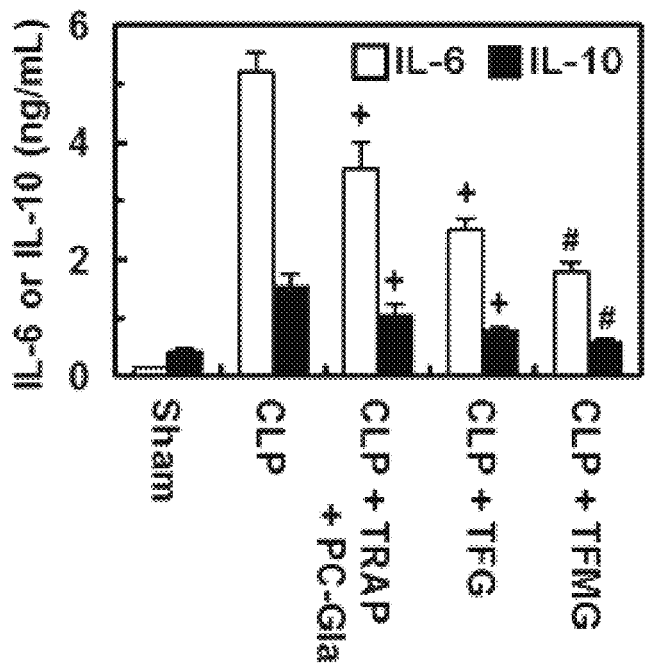
FIG. 18A and FIG. 18B show the results of evaluating the levels of inflammatory cytokines in blood after TFG administration, TFMG administration, and co-administration of TRAP and PC-Gla to an animal model of CLP-induced sepsis (FIG. 18A: IL-6, IL-10.
Figure 18B:
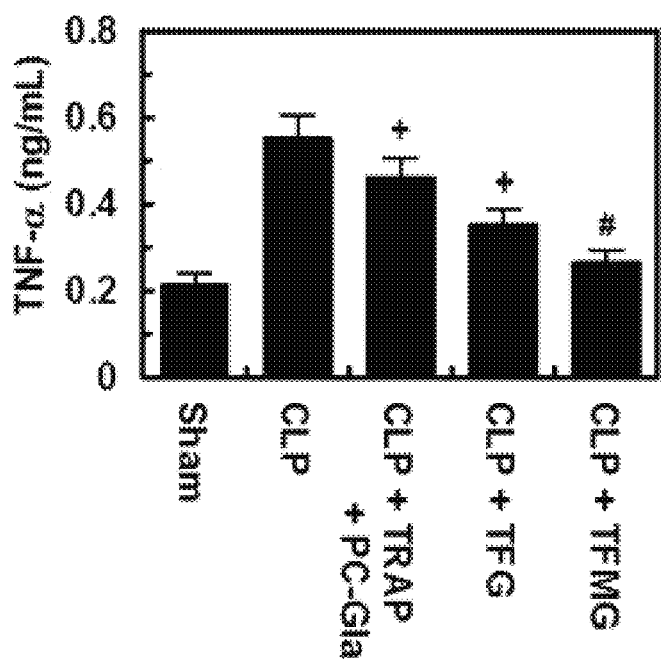

First, a solid-phase ELISA was used to measure the binding affinity of TFG or TFMG toward the PC-Gla receptor, EPCR. In this assay, the effciency of their binding to soluble EPCR (sEPCR) was compared. As shown in FIG. 9, wild type PC bound to sEPCR, with a $K_{d(app)}$ of approximately 31.3 nM, which is similar to previously reported binding afinity for PC to sEPCR (29 nM) in an aqueous solution. $K_{d(app)}$ of 32.0, 31.5 and 307 nM were obtained for the interaction between sEPCR and PC-Gla peptide, TFG and TFMG, respectively. These data suggest that each of TFG and TFMG construct could bind to EPCR as strongly as wild-type PC.

Subsequently, the present inventors evaluated the degree of binding of PC-Gla, TFG and TFMG to HUVECs, respectively, and found that TFG and TFMG exhibited strong binding affinities which are equivalent to that of PC-Gla binding to HUVECs (FIG. 10). This suggests that binding to HUVEC was enhanced by TRAP which binds to PAR-1.

The in vivo binding activities of TFG and TTMG were verified by immunohistochemistry, showing that injected TFG and TFMG were colocalized with EPCR and CD31 in the mouse vena cava. in addition, their binding seemed to be dominant over that of PC-Gla (FIG. 11).

Next, the present inventors compared in vitro and in vivo binding of TFG and TFMG to endothelial cells with that of PC-Gla. As a result, as shown in FIG. 12A & FIG. 12B, it was confirmed that TFG and TFMG bound more strongly to, and stayed longer on, endothelial cells than PC-Gla did in both in vivo and in vitro.

The present inventors also assessed the ability of TRAP peptides, TFG and TFMG to activate PAR-1. As shown in FIG. 13, the data showed strong similarities in the PAR-1 cleavage activities of TRAP peptides, TFG, and TFMG.

Example 4

Evaluation of Efficacy in Animal Models of CLP-Induced Sepsis

Based on the above described experimental results, the present inventors expected that TFG and TFMG would exhibit an excellent efficacy in an animal model of CLP-induced sepsis, and that TFG and TFMG would exhibit a better efficacy than the co-administration of PC-Gla and TRAP.

(1) Assessment of Survival Rate

As a result of TFG administration, TFMG administration or co-administration of PC-Gla and TRAP to an animal model of CLP-induced sepsis, as shown in FIG. 14, the survival rate was significantly improved in the TFG or TFMG administration groups, in comparison with the PC-Gla and TRAP co-administration group.

(2) Assessment of the Degree of Tissue Edema and Lung Tissue Damage

Meanwhile, as shown in FIG. 15, in an animal model of CLP-induced sepsis, interstitial edema with massive infiltration of inflammatory cells into the interstitium and alveolar spaces were observed and the pulmonary architecture was severely damaged. However, these pathologic conditions were significantly alleviated by TFG administration, TFMG administration or co-administration of PC-Gla and TRAP. Especially, TFG administration or TFMG administration was found to be more effective than the co-administration of PC-Gla and TRAP. In addition, the TFG administration or TFMG administration group showed a significantly superior effect in terms of a histopathologic score of pulmonary injury, in comparison with the co-administration of PC-Gla and TRAP (FIG. 16).

(3) Assessment of General Indicators on Organ Toxicity

Systemic inflammation during sepsis frequently causes multiple organ failure, in which the liver and kidneys are major target organs.

As seen in FIG. 17A, FIG. 17B, FIG. 17C and FIG. 17D, it was observed in the animal model of CLP-induced sepsis that the levels of ALT and AST (markers of hepatic injury) were greatly increased, while those of creatinine and BUN levels (markers of renal injury) were also significantly increased. In addition, the level of LDH, which is another marker of general organ injury, increased significantly in the sepsis animal model. It was found that the toxicity indicators for liver, kidneys, and general organs were considerably improved by TFG administration, TFMG administration or co-administration of PC-Gla and TRAP. In particular, it was confirmed that such an effect was particularly prominent in the TFG administration group and the TFMG administration group, respectively.

(4) Evaluation on the Level of Inflammatory Cytokine Secretion

The present inventors evaluated the levels of IL-6, IL-10 and TNF-α, inflammatory cytokines secreted during the course of sepsis. The IL-10 and TNF-α appear to be essential mediators of sepsis-induced vascular inflammation. IL-6 blockade with neutralizing antibodies has been shown to be an important protective mechanism against sepsis mortality.

As shown in FIG. 18A & FIG. 18B, the levels of IL-6, IL-10 and TNF-α were significantly increased in the CLP-induced sepsis animal model, which such a condition was mitigated by the TFG administration, TFMG administration or co-administration of PC-Gla and TRAP, respectively. Especially, it was confirmed that such an effect was remarkably excellent in the TFG- and TFMG-treated groups.

Taken together, the TFG- and TFMG-administered groups were found to be significantly effective in sepsis treatment in comparison with the PC-Gla and TRAP co-administered group, while TFMG was more effective antiseptic than TFG.

The above results suggest that the linker in TFMG was cleaved by MMP-2 at the inflammation pathological site to release PC-Gla and the released PC-Gla then independently exhibits its physiological activity, while TFMG following the release of PC-Gla was able to exhibit TRAP activity superior to that of TFG due to a reduction in the steric hindrance.

Example 5

Assessment of Endothelial Cell Permeability

During severe vascular inflammatory reactions, overexpression of inflammatory cytokines/chemokines may irreversibly damage vascular integrity, and cause excessive circulatory fluid loss. This may lead to prolonged tissue hypoperfusion, organ dysfunction, and ultimately death. Therefore, vascular permeability plays a pivotal role in severe vascular inflammatory diseases.

Figure 19:
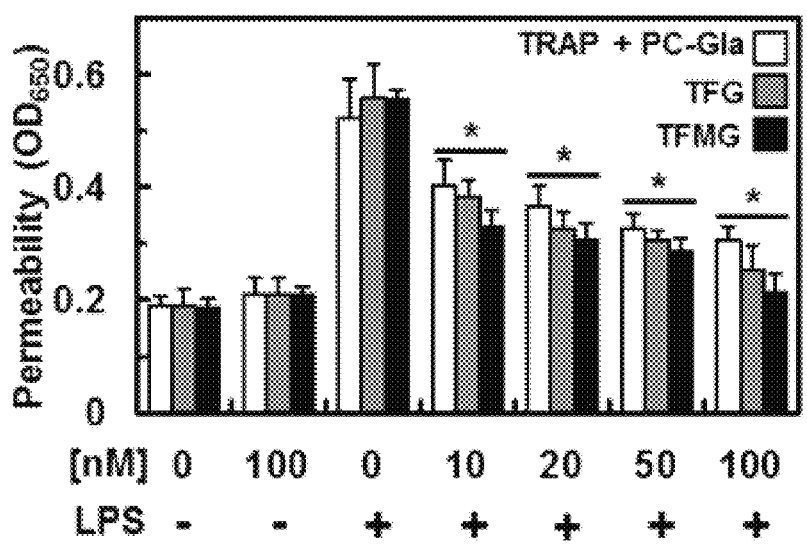
FIG. 19 shows the results of measuring the permeability after TFG administration, TFMG administration and co-administration of TRAP and PC-Gla to LPS-stimulated HUVEC cells, respectively.
Figure 20:
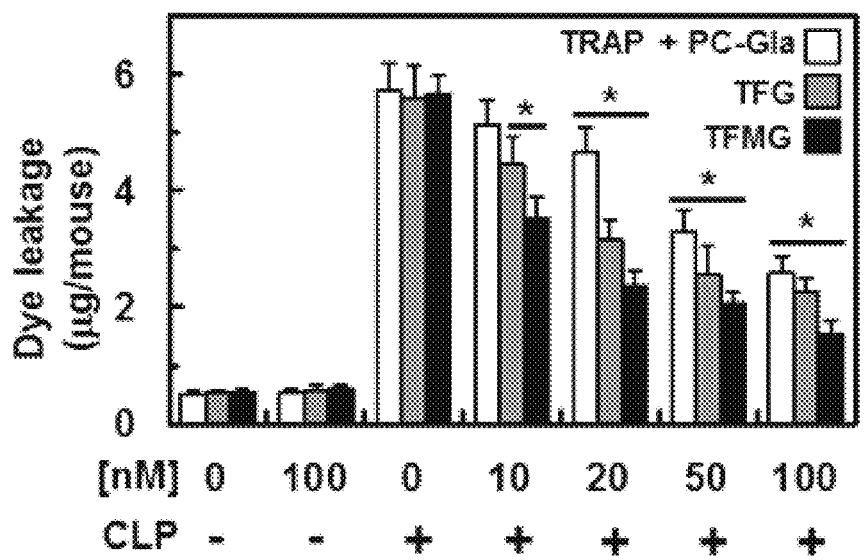
FIG. 20 shows the result of evaluating vascular permeability after TFG administration, TFMG administration and co-administration of TRAP and PC-Gla to an animal model of CLP-induced sepsis, respectively.

Results of evaluating in vitro and in vivo endothelial cell permeability by the TFG administration, TFMG administration or co-administration of PC-Gla and TRAP are shown in FIG. 19 and FIG. 20. It was found that LPS or CLP induction significantly increased the permeability in HUVECs and mice, and that this phenomenon was alleviated by the TFG administration, TFMG administration or co-administration of PC-Gla and TRAP, respectively.

Example 6

Assessment of the Expression of Cell Adhesion Factor (CAM) and the Migration of Leukocytes The vascular inflammatory responses are known to be mediated by the increased expression of CAMs such as ICAM-1, VCAM-1 and E-selection on the surfaces of endothelial cells, thereby promoting the adhesion and migration of leukocytes across the endothelium to the sites of inflammation. Transendothelial migration of circulating leukocytes to the vascular endothelium is a fundamental step during the pathogenesis of vascular inflammatory diseases.

Figure 21A:
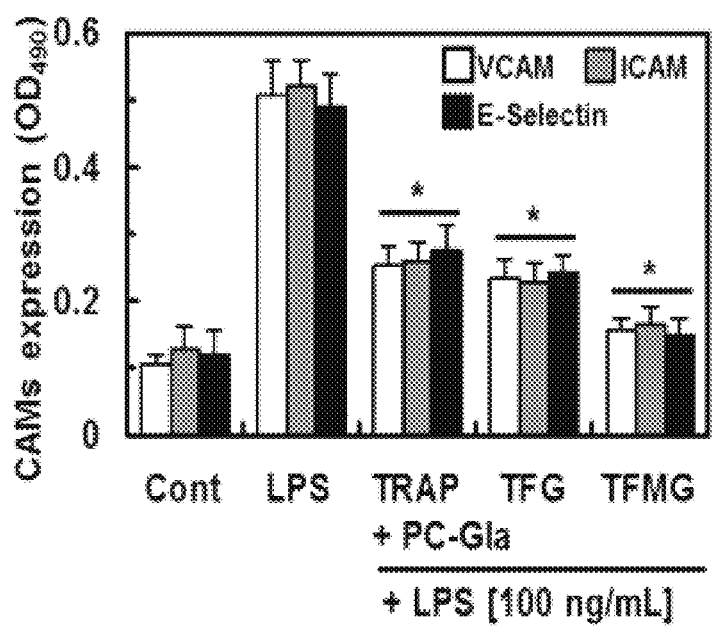
FIG. 21A and FIG. 21B show the results of evaluating the expression level of vascular cell adhesion factor-1 (VCAM-1) and the adhesion amount of leukocyte after TFG administration, TFMG administration and co-administration of TRAP and PC-Gla to LPS-stimulated HUVEC cells, respectively.
Figure 21B:
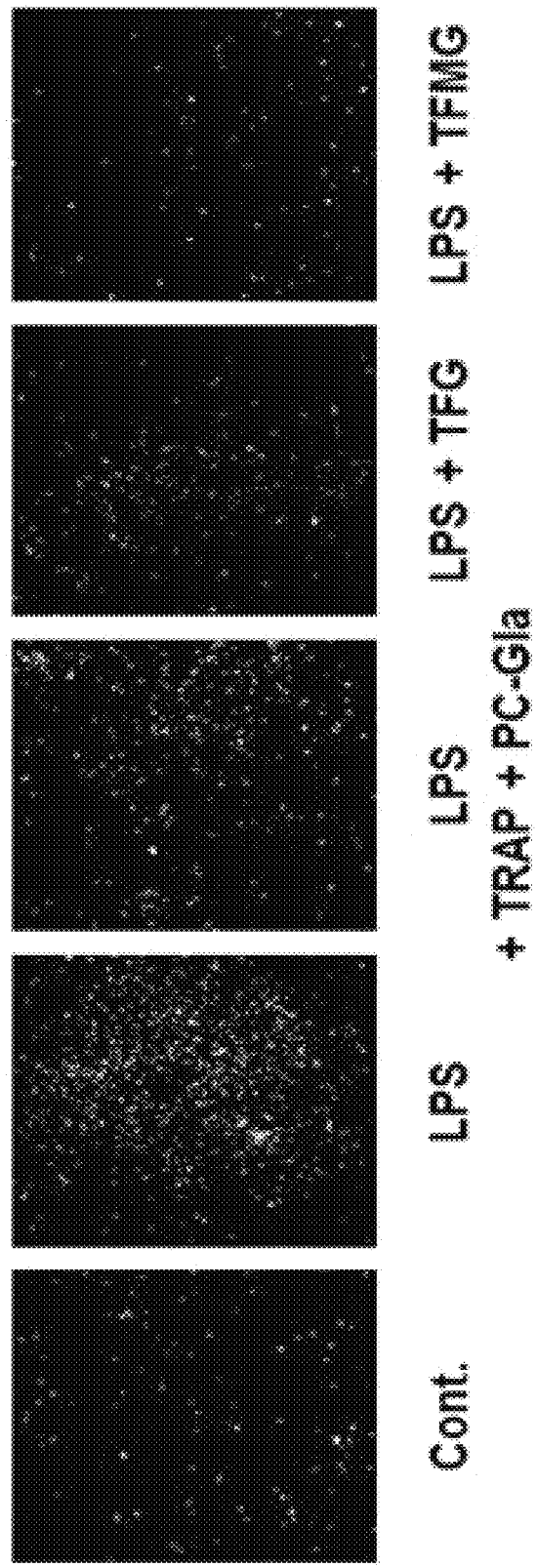
Figure 22:
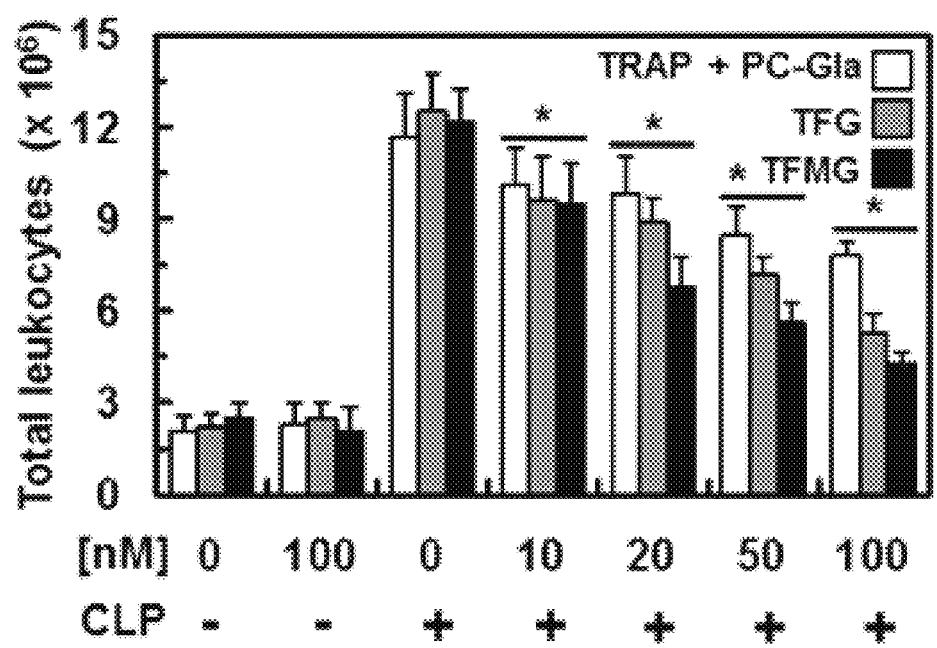
FIG. 22 shows the results of evaluating the amount of leukocyte movement after TFG administration, TFMG administration, and co-administration of TRAP and PC-Gla to an animal model with CLP-induced sepsis, respectively.

It was observed that TFMG and TFG inhibited the LPS-mediated upregulation of CAMs (FIG. 21A), adhesion of leukocytes (FIG. 21B), and CLP-mediated migration of leukocytes (FIG. 22). The above results demonstrate the potential of TFMG and TFG for treating vascular inflammatory diseases.

INDUSTRIAL APPLICABILITY

As described above, there is provided a fusion polypeptide, in which an anti-inflammatory polypeptide is fused to a N-terminus and/or a C-terminus of a human-derived ferritin monomer fragment having an amino acid sequence of SEQ ID NO: 1, may fuse two types of anti-inflammatory polypeptides which act through different mechanisms, respectively, into a nanocage for administration, thus the fusion polypeptide exhibiting an excellent effect in the treatment of an inflammatory disease including sepsis to be highly industrially applicable.

What is claimed is:

1. A fusion polypeptide comprising the amino acid sequence of SEQ ID NO: 14 or SEQ ID NO: 15.

2. A polynucleotide encoding the fusion polypeptide of claim 1.

3. An expression vector comprising the polynucleotide of claim 2.

4. A transformant transformed with the expression vector of claim 3.

5. A protein cage comprising the fusion polypeptide of claim 1, wherein an anti-inflammatory polypeptide protrudes outside the protein cage.

6. A pharmaceutical composition, the composition comprising the fusion polypeptide of claim 1 as an active ingredient.

7. A method for treating an inflammatory disease in a subject in need thereof, the method comprising administering an effective amount of a composition comprising the fusion polypeptide of claim 1 as an active ingredient to the subject in need thereof.

8. The method of claim 7, wherein the inflammatory disease is selected from the group consisting of inflammatory bowel disease, diabetic eye disease, peritonitis, osteomyelitis, cellulitis, meningitis, encephalitis, pancreatitis, traumatic shock, bronchial asthma, rhinitis, sinusitis, otitis, pneumonia, gastritis, enteritis, cystic fibrosis, apoplexy, bronchitis, bronchiolitis, hepatitis, nephritis, arthritis, gout, spondylitis, Reiter's syndrome, polyarteritis nodosa, irritable vasculitis, Lou Gehrig's granulomatosis, Polymyalgia rheumatica, arthritic arteritis, calcium crystal arthropathies, pseudogout, non-articular rheumatism, bursitis, tenosynovitis, epicondylitis (tennis elbow), neuropathic joint disease (Charcot's joint), hemarthrosis, Henoch-Schonlein purpura, hypertrophic osteoarthropathy, multicentric reticulohistiocytoma, surcoilosis, hemochromatosis, sickle cell disease and other hemochromatosis, hyperlipoproteinemia, hypogammaglobulinemia, hyperparathyroidism, acromegaly, familial Mediterranean fever, Behcet's disease, systemic lupus erythematosus, relapsing fever, psoriasis, multiple sclerosis, sepsis, septic shock, acute respiratory distress syndrome, multiple organ dysfunction syndrome, chronic obstructive pulmonary disease, acute lung injury and broncho-pulmonary dysplasia.

\* \* \* \* \*

SEQUENCE LISTING

```
<160> NUMBER OF SEQ ID NOS: 21

<210> SEQ ID NO 1
<211> LENGTH: 161
<212> TYPE: PRT
<213> ORGANISM: Artificial Sequence
<220> FEATURE:
<223> OTHER INFORMATION: Human ferritin heavy chain monomer fragment

<400> SEQUENCE: 1

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
        35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
        115                 120                 125
```

```
His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala

<210> SEQ ID NO 2
<211> LENGTH: 183
<212> TYPE: PRT
<213> ORGANISM: Artificial Sequence
<220> FEATURE:
<223> OTHER INFORMATION: Human ferritin heavy chain monomer

<400> SEQUENCE: 2

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
                20                  25                  30

Tyr Val Tyr Leu Ser Met Ser Tyr Tyr Phe Asp Arg Asp Asp Val Ala
            35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
            180

<210> SEQ ID NO 3
<211> LENGTH: 6
<212> TYPE: PRT
<213> ORGANISM: Artificial Sequence
<220> FEATURE:
<223> OTHER INFORMATION: Thrombin receptor agonist peptide (TRAP)

<400> SEQUENCE: 3

Thr Phe Leu Leu Arg Asn
1               5

<210> SEQ ID NO 4
<211> LENGTH: 45
<212> TYPE: PRT
<213> ORGANISM: Artificial Sequence
<220> FEATURE:
<223> OTHER INFORMATION: Protein C-Gla domain

<400> SEQUENCE: 4

Ala Asn Ser Phe Leu Glu Glu Leu Arg His Ser Ser Leu Glu Arg Glu
```

```
                 1               5                  10                 15
Cys Ile Glu Glu Ile Cys Asp Phe Glu Glu Ala Lys Glu Ile Phe Gln
                20                 25                 30

Asn Val Asp Asp Thr Leu Ala Phe Trp Ser Lys His Val
                35                 40                 45

<210> SEQ ID NO 5
<211> LENGTH: 67
<212> TYPE: PRT
<213> ORGANISM: Artificial Sequence
<220> FEATURE:
<223> OTHER INFORMATION: Human beta defensin-3

<400> SEQUENCE: 5

Met Arg Ile His Tyr Leu Leu Phe Ala Leu Leu Phe Leu Phe Leu Val
1               5                  10                 15

Pro Val Pro Gly His Gly Gly Ile Ile Asn Thr Leu Gln Lys Tyr Tyr
                20                 25                 30

Cys Arg Val Arg Gly Gly Arg Cys Ala Val Leu Ser Cys Leu Pro Lys
                35                 40                 45

Glu Glu Gln Ile Gly Lys Cys Ser Thr Arg Gly Arg Lys Cys Cys Arg
                50                 55                 60

Arg Lys Lys
65

<210> SEQ ID NO 6
<211> LENGTH: 177
<212> TYPE: PRT
<213> ORGANISM: Artificial Sequence
<220> FEATURE:
<223> OTHER INFORMATION: Interleukin-1 receptor antagonist

<400> SEQUENCE: 6

Met Glu Ile Cys Arg Gly Leu Arg Ser His Leu Ile Thr Leu Leu Leu
1               5                  10                 15

Phe Leu Phe His Ser Glu Thr Ile Cys Arg Pro Ser Gly Arg Lys Ser
                20                 25                 30

Ser Lys Met Gln Ala Phe Arg Ile Trp Asp Val Asn Gln Lys Thr Phe
                35                 40                 45

Tyr Leu Arg Asn Asn Gln Leu Val Ala Gly Tyr Leu Gln Gly Pro Asn
                50                 55                 60

Val Asn Leu Glu Glu Lys Ile Asp Val Val Pro Ile Glu Pro His Ala
65                 70                 75                 80

Leu Phe Leu Gly Ile His Gly Gly Lys Met Cys Leu Ser Cys Val Lys
                85                 90                 95

Ser Gly Asp Glu Thr Arg Leu Gln Leu Glu Ala Val Asn Ile Thr Asp
                100                105                110

Leu Ser Glu Asn Arg Lys Gln Asp Lys Arg Phe Ala Phe Ile Arg Ser
                115                120                125

Asp Ser Gly Pro Thr Thr Ser Phe Glu Ser Ala Ala Cys Pro Gly Trp
                130                135                140

Phe Leu Cys Thr Ala Met Glu Ala Asp Gln Pro Val Ser Leu Thr Asn
145                150                155                160

Met Pro Asp Glu Gly Val Met Val Thr Lys Phe Tyr Phe Gln Glu Asp
                165                170                175

Glu
```

```
<210> SEQ ID NO 7
<211> LENGTH: 137
<212> TYPE: PRT
<213> ORGANISM: Artificial Sequence
<220> FEATURE:
<223> OTHER INFORMATION: Interleukin-4

<400> SEQUENCE: 7

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Asn Thr Thr
        35                  40                  45

Glu Lys Glu Thr Phe Cys Arg Ala Ala Thr Val Leu Arg Gln Phe Tyr
    50                  55                  60

Ser His His Glu Lys Asp Thr Arg Cys Leu Gly Ala Thr Ala Gln Gln
65                  70                  75                  80

Phe His Arg His Lys Gln Leu Ile Arg Phe Leu Lys Arg Leu Asp Arg
                85                  90                  95

Asn Leu Trp Gly Leu Ala Gly Leu Asn Ser Cys Pro Val Lys Glu Ala
            100                 105                 110

Asn Gln Ser Thr Leu Glu Asn Phe Leu Glu Arg Leu Lys Thr Ile Met
        115                 120                 125

Arg Glu Lys Tyr Ser Lys Cys Ser Ser
    130                 135

<210> SEQ ID NO 8
<211> LENGTH: 199
<212> TYPE: PRT
<213> ORGANISM: Artificial Sequence
<220> FEATURE:
<223> OTHER INFORMATION: Interleukin-11

<400> SEQUENCE: 8

Met Asn Cys Val Cys Arg Leu Val Leu Val Val Leu Ser Leu Trp Pro
1               5                   10                  15

Asp Thr Ala Val Ala Pro Gly Pro Pro Gly Pro Pro Arg Val Ser
            20                  25                  30

Pro Asp Pro Arg Ala Glu Leu Asp Ser Thr Val Leu Leu Thr Arg Ser
        35                  40                  45

Leu Leu Ala Asp Thr Arg Gln Leu Ala Ala Gln Leu Arg Asp Lys Phe
    50                  55                  60

Pro Ala Asp Gly Asp His Asn Leu Asp Ser Leu Pro Thr Leu Ala Met
65                  70                  75                  80

Ser Ala Gly Ala Leu Gly Ala Leu Gln Leu Pro Gly Val Leu Thr Arg
                85                  90                  95

Leu Arg Ala Asp Leu Leu Ser Tyr Leu Arg His Val Gln Trp Leu Arg
            100                 105                 110

Arg Ala Gly Gly Ser Ser Leu Lys Thr Leu Glu Pro Glu Leu Gly Thr
        115                 120                 125

Leu Gln Ala Arg Leu Asp Arg Leu Leu Arg Arg Leu Gln Leu Leu Met
    130                 135                 140

Ser Arg Leu Ala Leu Pro Gln Pro Pro Asp Pro Pro Ala Pro Pro
145                 150                 155                 160

Leu Ala Pro Pro Ser Ser Ala Trp Gly Gly Ile Arg Ala Ala His Ala
                165                 170                 175
```

```
Ile Leu Gly Gly Leu His Leu Thr Leu Asp Trp Ala Val Arg Gly Leu
            180                 185                 190

Leu Leu Leu Lys Thr Arg Leu
        195

<210> SEQ ID NO 9
<211> LENGTH: 131
<212> TYPE: PRT
<213> ORGANISM: Artificial Sequence
<220> FEATURE:
<223> OTHER INFORMATION: Interleukin-13

<400> SEQUENCE: 9

Met Ala Leu Leu Leu Thr Thr Val Ile Ala Leu Thr Cys Leu Gly Gly
1               5                   10                  15

Phe Ala Ser Pro Gly Pro Val Pro Ser Thr Ala Leu Arg Glu Leu
            20                  25                  30

Ile Glu Glu Leu Val Asn Ile Thr Gln Asn Gln Lys Arg Pro Leu Cys
        35                  40                  45

Asn Gly Ser Met Val Trp Ser Ile Asn Leu Thr Ala Gly Met Tyr Cys
    50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Phe Ser Ser Leu His Val Arg Asp Thr Lys Ile Glu Val Ala Gln
            100                 105                 110

Phe Val Lys Asp Leu Leu Leu His Leu Lys Lys Leu Phe Arg Glu Gly
        115                 120                 125

Arg Phe Asn
    130

<210> SEQ ID NO 10
<211> LENGTH: 277
<212> TYPE: PRT
<213> ORGANISM: Artificial Sequence
<220> FEATURE:
<223> OTHER INFORMATION: TNF-alpha stimulated gene 6 protein

<400> SEQUENCE: 10

Met Ile Ile Leu Ile Tyr Leu Phe Leu Leu Trp Glu Asp Thr Gln
1               5                   10                  15

Gly Trp Gly Phe Lys Asp Gly Ile Phe His Asn Ser Ile Trp Leu Glu
            20                  25                  30

Arg Ala Ala Gly Val Tyr His Arg Glu Ala Arg Ser Gly Lys Tyr Lys
        35                  40                  45

Leu Thr Tyr Ala Glu Ala Lys Ala Val Cys Glu Phe Glu Gly Gly His
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
        115                 120                 125

Asn Pro His Ala Lys Glu Cys Gly Gly Val Phe Thr Asp Pro Lys Gln
    130                 135                 140
```

```
Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Pro Gly Cys Leu Ala Asp Tyr
            180                 185                 190

Val Glu Ile Tyr Asp Ser Tyr Asp Val His Gly Phe Val Gly Arg
        195                 200                 205

Tyr Cys Gly Asp Glu Leu Pro Asp Ile Ile Ser Thr Gly Asn Val
    210                 215                 220

Met Thr Leu Lys Phe Leu Ser Asp Ala Ser Val Thr Ala Gly Phe
225                 230                 235                 240

Gln Ile Lys Tyr Val Ala Met Asp Pro Val Ser Lys Ser Ser Gln Gly
                245                 250                 255

Lys Asn Thr Ser Thr Thr Ser Thr Gly Asn Lys Asn Phe Leu Ala Gly
            260                 265                 270

Arg Phe Ser His Leu
        275

<210> SEQ ID NO 11
<211> LENGTH: 461
<212> TYPE: PRT
<213> ORGANISM: Artificial Sequence
<220> FEATURE:
<223> OTHER INFORMATION: Activated protein C

<400> SEQUENCE: 11

Met Trp Gln Leu Thr Ser Leu Leu Leu Phe Val Ala Thr Trp Gly Ile
1               5                   10                  15

Ser Gly Thr Pro Ala Pro Leu Asp Ser Val Phe Ser Ser Glu Arg
            20                  25                  30

Ala His Gln Val Leu Arg Ile Arg Lys Arg Ala Asn Ser Phe Leu Glu
        35                  40                  45

Glu Leu Arg His Ser Ser Leu Glu Arg Glu Cys Ile Glu Glu Ile Cys
50                  55                  60

Asp Phe Glu Glu Ala Lys Glu Ile Phe Gln Asn Val Asp Asp Thr Leu
65                  70                  75                  80

Ala Phe Trp Ser Lys His Val Asp Gly Asp Gln Cys Leu Val Leu Pro
                85                  90                  95

Leu Glu His Pro Cys Ala Ser Leu Cys Cys Gly His Gly Thr Cys Ile
            100                 105                 110

Asp Gly Ile Gly Ser Phe Ser Cys Asp Cys Arg Ser Gly Trp Glu Gly
        115                 120                 125

Arg Phe Cys Gln Arg Glu Val Ser Phe Leu Asn Cys Ser Leu Asp Asn
130                 135                 140

Gly Gly Cys Thr His Tyr Cys Leu Glu Glu Val Gly Trp Arg Arg Cys
145                 150                 155                 160

Ser Cys Ala Pro Gly Tyr Lys Leu Gly Asp Asp Leu Leu Gln Cys His
                165                 170                 175

Pro Ala Val Lys Phe Pro Cys Gly Arg Pro Trp Lys Arg Met Glu Lys
            180                 185                 190

Lys Arg Ser His Leu Lys Arg Asp Thr Glu Asp Gln Glu Asp Gln Val
        195                 200                 205

Asp Pro Arg Leu Ile Asp Gly Lys Met Thr Arg Arg Gly Asp Ser Pro
210                 215                 220
```

```
Trp Gln Val Val Leu Leu Asp Ser Lys Lys Lys Leu Ala Cys Gly Ala
225                 230                 235                 240

Val Leu Ile His Pro Ser Trp Val Leu Thr Ala Ala His Cys Met Asp
                245                 250                 255

Glu Ser Lys Lys Leu Leu Val Arg Leu Gly Glu Tyr Asp Leu Arg Arg
            260                 265                 270

Trp Glu Lys Trp Glu Leu Asp Leu Asp Ile Lys Glu Val Phe Val His
        275                 280                 285

Pro Asn Tyr Ser Lys Ser Thr Thr Asp Asn Asp Ile Ala Leu Leu His
    290                 295                 300

Leu Ala Gln Pro Ala Thr Leu Ser Gln Thr Ile Val Pro Ile Cys Leu
305                 310                 315                 320

Pro Asp Ser Gly Leu Ala Glu Arg Glu Leu Asn Gln Ala Gly Gln Glu
                325                 330                 335

Thr Leu Val Thr Gly Trp Gly Tyr His Ser Ser Arg Glu Lys Glu Ala
            340                 345                 350

Lys Arg Asn Arg Thr Phe Val Leu Asn Phe Ile Lys Ile Pro Val Val
        355                 360                 365

Pro His Asn Glu Cys Ser Glu Val Met Ser Asn Met Val Ser Glu Asn
    370                 375                 380

Met Leu Cys Ala Gly Ile Leu Gly Asp Arg Gln Asp Ala Cys Glu Gly
385                 390                 395                 400

Asp Ser Gly Gly Pro Met Val Ala Ser Phe His Gly Thr Trp Phe Leu
                405                 410                 415

Val Gly Leu Val Ser Trp Gly Glu Gly Cys Gly Leu Leu His Asn Tyr
            420                 425                 430

Gly Val Tyr Thr Lys Val Ser Arg Tyr Leu Asp Trp Ile His Gly His
        435                 440                 445

Ile Arg Asp Lys Glu Ala Pro Gln Lys Ser Trp Ala Pro
    450                 455                 460

<210> SEQ ID NO 12
<211> LENGTH: 249
<212> TYPE: PRT
<213> ORGANISM: Artificial Sequence
<220> FEATURE:
<223> OTHER INFORMATION: Parotid secreted protein

<400> SEQUENCE: 12

Met Leu Gln Leu Trp Lys Leu Val Leu Leu Cys Gly Val Leu Thr Gly
1               5                   10                  15

Thr Ser Glu Ser Leu Leu Asp Asn Leu Gly Asn Asp Leu Ser Asn Val
            20                  25                  30

Val Asp Lys Leu Glu Pro Val Leu His Glu Gly Leu Glu Thr Val Asp
        35                  40                  45

Asn Thr Leu Lys Gly Ile Leu Glu Lys Leu Lys Val Asp Leu Gly Val
    50                  55                  60

Leu Gln Lys Ser Ser Ala Trp Gln Leu Ala Lys Gln Lys Ala Gln Glu
65                  70                  75                  80

Ala Glu Lys Leu Leu Asn Asn Val Ile Ser Lys Leu Leu Pro Thr Asn
                85                  90                  95

Thr Asp Ile Phe Gly Leu Lys Ile Ser Asn Ser Leu Ile Leu Asp Val
            100                 105                 110

Lys Ala Glu Pro Ile Asp Asp Gly Lys Gly Leu Asn Leu Ser Phe Pro
        115                 120                 125
```

```
Val Thr Ala Asn Val Thr Val Ala Gly Pro Ile Ile Gly Gln Ile Ile
    130                 135                 140

Asn Leu Lys Ala Ser Leu Asp Leu Leu Thr Ala Val Thr Ile Glu Thr
145                 150                 155                 160

Asp Pro Gln Thr His Gln Pro Val Ala Val Leu Arg Glu Cys Ala Ser
                165                 170                 175

Asp Pro Thr Ser Ile Ser Leu Ser Leu Leu Asp Lys His Ser Gln Ile
            180                 185                 190

Ile Asn Lys Phe Val Asn Ser Val Ile Asn Thr Leu Lys Ser Thr Val
        195                 200                 205

Ser Ser Leu Leu Gln Lys Glu Ile Cys Pro Leu Ile Arg Ile Phe Ile
210                 215                 220

His Ser Leu Asp Val Asn Val Ile Gln Gln Val Val Asp Asn Pro Gln
225                 230                 235                 240

His Lys Thr Gln Leu Gln Thr Leu Ile
                245

<210> SEQ ID NO 13
<211> LENGTH: 7
<212> TYPE: PRT
<213> ORGANISM: Artificial Sequence
<220> FEATURE:
<223> OTHER INFORMATION: Linker comprising MMP-2 cleavage site

<400> SEQUENCE: 13

Gly Pro Leu Gly Leu Ala Gly
1               5

<210> SEQ ID NO 14
<211> LENGTH: 237
<212> TYPE: PRT
<213> ORGANISM: Artificial Sequence
<220> FEATURE:
<223> OTHER INFORMATION: Fusion polypeptide (1)

<400> SEQUENCE: 14

Met Gly Gly Thr Thr Phe Leu Leu Arg Asn Ala Ser Gly His Met Ser
1               5                   10                  15

Ser Gln Ile Arg Gln Asn Tyr Ser Thr Asp Val Glu Ala Ala Val Asn
            20                  25                  30

Ser Leu Val Asn Leu Tyr Leu Gln Ala Ser Tyr Thr Tyr Leu Ser Leu
        35                  40                  45

Gly Phe Tyr Phe Asp Arg Asp Asp Val Ala Leu Glu Gly Val Ser His
    50                  55                  60

Phe Phe Arg Glu Leu Ala Glu Glu Lys Arg Glu Gly Tyr Glu Arg Leu
65                  70                  75                  80

Leu Lys Met Gln Asn Gln Arg Gly Gly Arg Ile Phe Leu Gln Asp Ile
                85                  90                  95

Lys Lys Pro Ala Glu Asp Glu Trp Gly Lys Thr Pro Asp Ala Met Lys
            100                 105                 110

Ala Ala Met Ala Leu Glu Lys Lys Leu Asn Gln Ala Leu Leu Asp Leu
        115                 120                 125

His Ala Leu Gly Ser Ala Arg Thr Asp Pro His Leu Cys Asp Phe Leu
    130                 135                 140

Glu Thr His Phe Leu Asp Glu Glu Val Lys Leu Ile Lys Lys Met Gly
145                 150                 155                 160

Asp His Leu Thr Asn Leu His Arg Leu Gly Gly Gly Ser Glu Phe Val
```

```
                     165                 170                 175

Asp Gly Gly Gly Ser Gly Thr Ser Ala Asn Ser Phe Leu Glu Glu Leu
                 180                 185                 190

Arg His Ser Ser Leu Glu Arg Glu Cys Ile Glu Glu Ile Cys Asp Phe
             195                 200                 205

Glu Glu Ala Lys Glu Ile Phe Gln Asn Val Asp Asp Thr Leu Ala Phe
         210                 215                 220

Trp Ser Lys His Val Leu Glu His His His His His His
225                 230                 235
```

<210> SEQ ID NO 15
<211> LENGTH: 244
<212> TYPE: PRT
<213> ORGANISM: Artificial Sequence
<220> FEATURE:
<223> OTHER INFORMATION: Fusion polypeptide (2)

<400> SEQUENCE: 15

```
Met Gly Gly Thr Thr Phe Leu Leu Arg Asn Ala Ser Gly His Met Ser
1               5                   10                  15

Ser Gln Ile Arg Gln Asn Tyr Ser Thr Asp Val Glu Ala Ala Val Asn
             20                  25                  30

Ser Leu Val Asn Leu Tyr Leu Gln Ala Ser Tyr Thr Tyr Leu Ser Leu
         35                  40                  45

Gly Phe Tyr Phe Asp Arg Asp Asp Val Ala Leu Glu Gly Val Ser His
     50                  55                  60

Phe Phe Arg Glu Leu Ala Glu Glu Lys Arg Glu Gly Tyr Glu Arg Leu
65                  70                  75                  80

Leu Lys Met Gln Asn Gln Arg Gly Gly Arg Ile Phe Leu Gln Asp Ile
                 85                  90                  95

Lys Lys Pro Ala Glu Asp Glu Trp Gly Lys Thr Pro Asp Ala Met Lys
             100                 105                 110

Ala Ala Met Ala Leu Glu Lys Lys Leu Asn Gln Ala Leu Leu Asp Leu
         115                 120                 125

His Ala Leu Gly Ser Ala Arg Thr Asp Pro His Leu Cys Asp Phe Leu
     130                 135                 140

Glu Thr His Phe Leu Asp Glu Glu Val Lys Leu Ile Lys Lys Met Gly
145                 150                 155                 160

Asp His Leu Thr Asn Leu His Arg Leu Gly Gly Ser Glu Phe Val
                 165                 170                 175

Asp Gly Gly Gly Ser Gly Thr Ser Gly Pro Leu Gly Leu Ala Gly Ala
             180                 185                 190

Asn Ser Phe Leu Glu Glu Leu Arg His Ser Ser Leu Glu Arg Glu Cys
         195                 200                 205

Ile Glu Glu Ile Cys Asp Phe Glu Glu Ala Lys Glu Ile Phe Gln Asn
     210                 215                 220

Val Asp Asp Thr Leu Ala Phe Trp Ser Lys His Val Leu Glu His His
225                 230                 235                 240

His His His His
```

<210> SEQ ID NO 16
<211> LENGTH: 20
<212> TYPE: DNA
<213> ORGANISM: Artificial Sequence
<220> FEATURE:
<223> OTHER INFORMATION: TRAP forward

```
<400> SEQUENCE: 16
cacttttctt cttcggaacg                                               20

<210> SEQ ID NO 17
<211> LENGTH: 28
<212> TYPE: DNA
<213> ORGANISM: Artificial Sequence
<220> FEATURE:
<223> OTHER INFORMATION: TRAP reverse

<400> SEQUENCE: 17
ctagcgttcc gaagaagaaa agtggtac                                      28

<210> SEQ ID NO 18
<211> LENGTH: 28
<212> TYPE: DNA
<213> ORGANISM: Artificial Sequence
<220> FEATURE:
<223> OTHER INFORMATION: PC-Gla domain forward

<400> SEQUENCE: 18
gaaactagtg ccaactcctt cctggagg                                      28

<210> SEQ ID NO 19
<211> LENGTH: 25
<212> TYPE: DNA
<213> ORGANISM: Artificial Sequence
<220> FEATURE:
<223> OTHER INFORMATION: PC-Gla domain reverse

<400> SEQUENCE: 19
gaactcgagg acgtgcttgg accag                                         25

<210> SEQ ID NO 20
<211> LENGTH: 46
<212> TYPE: DNA
<213> ORGANISM: Artificial Sequence
<220> FEATURE:
<223> OTHER INFORMATION: MMP-2 cleavage site forward

<400> SEQUENCE: 20
gaaactagtg gtcctctagg tctagccggt gccaactcct tcctgg                  46

<210> SEQ ID NO 21
<211> LENGTH: 25
<212> TYPE: DNA
<213> ORGANISM: Artificial Sequence
<220> FEATURE:
<223> OTHER INFORMATION: MMP-2 cleavage site reverse

<400> SEQUENCE: 21
gaactcgagg acgtgcttgg accag                                         25
```